US011678905B2

(12) United States Patent
Look et al.

(10) Patent No.: US 11,678,905 B2
(45) Date of Patent: Jun. 20, 2023

(54) SYSTEMS AND METHODS FOR REMOVAL OF BLOOD AND THROMBOTIC MATERIAL

(71) Applicant: WALK VASCULAR, LLC, Irvine, CA (US)

(72) Inventors: David M. Look, Newport Beach, CA (US); Bradley S. Culbert, Mission Viejo, CA (US)

(73) Assignee: WALK VASCULAR, LLC, Irvine, CA (US)

( * ) Notice: Subject to any disclaimer, the term of this patent is extended or adjusted under 35 U.S.C. 154(b) by 307 days.

(21) Appl. No.: 16/516,190

(22) Filed: Jul. 18, 2019

(65) Prior Publication Data

US 2020/0022711 A1 Jan. 23, 2020

Related U.S. Application Data

(60) Provisional application No. 62/700,763, filed on Jul. 19, 2018.

(51) Int. Cl.
*A61B 17/22* (2006.01)
*A61M 1/00* (2006.01)
(Continued)

(52) U.S. Cl.
CPC ........ *A61B 17/32037* (2013.01); *A61B 17/22* (2013.01); *A61M 1/64* (2021.05);
(Continued)

(58) Field of Classification Search
CPC .......... A61B 17/22; A61B 2017/22079; A61B 17/32; A61B 17/320016; A61B 17/32002;
(Continued)

(56) References Cited

U.S. PATENT DOCUMENTS 1,114,268 A 10/1914 Kells
1,144,268 A 6/1915 Vickery
(Continued)

FOREIGN PATENT DOCUMENTS

CN 1120805 A 4/1996
CN 201079629 Y 7/2008
(Continued)

OTHER PUBLICATIONS

Metzler, L., "Miniature Sensor Combines with Micropump to Control Drug Delivery", Medical Design Technology, Mar. 2017, pp. 22-23, MDTmag.com, Advantage Business Media, Rockaway, USA.
(Continued)

*Primary Examiner* — Kai H Weng
*Assistant Examiner* — Brandon W. Levy
(74) *Attorney, Agent, or Firm* — Workman Nydegger; Randy Shen

(57) ABSTRACT

A method for improving a flow condition through a catheter inserting a distal end of a sheath within the vasculature of a subject, placing the aspiration catheter through the sheath and advancing the aspiration catheter such that an open distal end of the aspiration lumen is distal to a distal end of the sheath and is in proximity to a thrombus within a blood vessel of a subject, coupling an extension conduit in fluid communication with a lumen of the sheath to a second fluid source, and activating a pump such that pressurized fluid from the first fluid source is applied to the supply lumen of the aspiration catheter, wherein when an active flowing condition is not present, fluid from the second fluid source is caused to flow through the lumen of the sheath.

20 Claims, 6 Drawing Sheets

(51) Int. Cl.
*A61B 17/3203* (2006.01)
*A61M 39/22* (2006.01)
*A61M 25/06* (2006.01)

(52) U.S. Cl.
CPC ............... *A61M 1/67* (2021.05); *A61M 1/72* (2021.05); *A61M 1/74* (2021.05); *A61M 1/741* (2021.05); *A61M 1/743* (2021.05); *A61M 1/81* (2021.05); *A61M 1/815* (2021.05); *A61M 1/84* (2021.05); *A61B 2017/22079* (2013.01); *A61M 25/0662* (2013.01); *A61M 39/22* (2013.01)

(58) Field of Classification Search
CPC .... A61B 17/320036; A61B 17/320068; A61B 17/320092; A61B 17/3201; A61B 17/3203; A61B 17/32037; A61B 17/3205; A61B 17/32053; A61B 17/32056; A61B 17/3207; A61B 17/320708; A61B 17/320725; A61B 17/32075; A61B 17/320758; A61B 17/320783; A61B 2217/005; A61B 2017/22067; A61B 2017/22038; A61B 2017/22082; A61B 2217/007; A61B 2017/320716; A61B 2017/1205; A61B 2017/00778; A61B 17/22012; A61B 17/22004; A61B 2017/2215; A61M 1/81; A61M 1/84; A61M 1/0001; A61M 1/0023; A61M 25/0662; A61M 39/22; A61M 1/90; A61M 1/65; A61M 1/66; A61M 1/67; A61M 1/68; A61M 1/682; A61M 1/684; A61M 1/98; A61M 1/982; A61M 1/984; A61M 1/985; A61M 1/71; A61M 31/005; A61M 2025/0024; A61M 25/0026; A61M 5/007; A61M 1/743; A61M 1/815; A61M 2205/12; A61M 1/0058; A61M 2205/3331; A61M 2210/12; A61M 1/72; A61M 1/74; A61M 2025/0681; A61M 1/60; A61M 1/64; A61M 25/0075; A61M 25/104; A61F 2/013
See application file for complete search history.

(56) References Cited

U.S. PATENT DOCUMENTS

| | | |
|---|---|---|
| 1,148,093 A | 7/1915 | Kells |
| 2,804,075 A | 8/1957 | Borden |
| 3,429,313 A | 2/1969 | Romanelli |
| 3,494,363 A | 2/1970 | Jackson |
| 3,589,363 A | 6/1971 | Banko et al. |
| 3,620,650 A | 11/1971 | Shaw |
| 3,631,847 A | 1/1972 | Hobbs |
| 3,693,613 A | 9/1972 | Kelman |
| 3,707,967 A | 1/1973 | Kitrilakis et al. |
| 3,748,435 A | 7/1973 | Reynolds |
| 3,807,401 A | 4/1974 | Bennett et al. |
| 3,818,913 A | 6/1974 | Wallach |
| 3,847,140 A | 11/1974 | Ayella |
| 3,916,892 A | 11/1975 | Latham, Jr. et al. |
| 3,918,453 A | 11/1975 | Leonard |
| 3,930,505 A | 1/1976 | Wallach |
| 3,955,573 A | 5/1976 | Hansen et al. |
| 4,030,503 A | 6/1977 | Clark, III |
| 4,274,411 A | 6/1981 | Dotson, Jr. |
| 4,299,221 A | 11/1981 | Phillips et al. |
| 4,465,470 A | 8/1984 | Kelman |
| 4,573,476 A | 3/1986 | Ruiz |
| 4,574,812 A | 3/1986 | Arkans |
| 4,638,539 A | 1/1987 | Palmer |
| 4,690,672 A | 9/1987 | Veltrup |
| 4,700,705 A | 10/1987 | Kensey et al. |
| 4,702,733 A | 10/1987 | Wright et al. |
| 4,715,853 A | 12/1987 | Prindle |
| 4,728,319 A | 3/1988 | Masch |
| 4,740,203 A | 4/1988 | Hoskins et al. |
| 4,747,821 A | 5/1988 | Kensey et al. |
| 4,747,834 A | 5/1988 | Prindle |
| 4,770,654 A | 9/1988 | Rogers et al. |
| 4,784,157 A | 11/1988 | Halls et al. |
| 4,790,813 A | 12/1988 | Kensey |
| 4,832,685 A | 5/1989 | Haines |
| 4,842,579 A | 6/1989 | Shiber |
| 4,854,325 A | 8/1989 | Stevens |
| 4,857,046 A | 8/1989 | Stevens et al. |
| 4,883,458 A | 11/1989 | Shiber |
| 4,883,467 A | 11/1989 | Franetzki et al. |
| 4,886,490 A | 12/1989 | Shiber |
| 4,886,507 A | 12/1989 | Patton et al. |
| 4,894,051 A | 1/1990 | Shiber |
| 4,898,574 A | 2/1990 | Uchiyama et al. |
| 4,957,482 A | 9/1990 | Shiber |
| 4,979,939 A | 12/1990 | Shiber |
| 4,998,919 A | 3/1991 | Schnepp-Pesch et al. |
| 5,002,553 A | 3/1991 | Shiber |
| 5,007,896 A | 4/1991 | Shiber |
| 5,011,468 A | 4/1991 | Lundquist et al. |
| 5,011,488 A | 4/1991 | Ginsburg |
| 5,024,651 A | 6/1991 | Shiber |
| 5,055,109 A | 10/1991 | Gould et al. |
| 5,057,098 A | 10/1991 | Zelman |
| 5,064,428 A | 11/1991 | Cope et al. |
| 5,073,164 A | 12/1991 | Hollister et al. |
| 5,073,168 A | 12/1991 | Danforth |
| 5,074,841 A | 12/1991 | Ademovic et al. |
| 5,078,722 A | 1/1992 | Stevens |
| 5,091,656 A | 2/1992 | Gahn |
| 5,125,893 A | 6/1992 | Dryden |
| 5,129,887 A | 7/1992 | Euteneuer et al. |
| 5,135,482 A | 8/1992 | Neracher |
| 5,135,531 A | 8/1992 | Shiber |
| 5,158,564 A | 10/1992 | Schnepp-Pesch et al. |
| 5,163,433 A | 11/1992 | Kagawa et al. |
| 5,195,954 A | 3/1993 | Schnepp-Pesch et al. |
| 5,197,795 A | 3/1993 | Mudrovich |
| 5,197,951 A | 3/1993 | Mahurkar |
| 5,234,407 A | 8/1993 | Teirstein et al. |
| 5,242,404 A | 9/1993 | Conley et al. |
| 5,243,997 A | 9/1993 | Uflacker et al. |
| 5,248,297 A | 9/1993 | Takase |
| 5,254,085 A | 10/1993 | Cleveland |
| 5,261,877 A | 11/1993 | Fine et al. |
| 5,284,486 A | 2/1994 | Kotula et al. |
| 5,290,247 A | 3/1994 | Crittenden |
| 5,306,244 A | 4/1994 | Shiber |
| 5,312,427 A | 5/1994 | Shturman |
| 5,318,518 A | 6/1994 | Plechinger et al. |
| 5,318,529 A | 6/1994 | Kontos |
| 5,320,604 A | 6/1994 | Walker et al. |
| 5,322,504 A | 6/1994 | Doherty et al. |
| 5,324,263 A | 6/1994 | Kraus et al. |
| 5,325,868 A | 7/1994 | Kimmelstiel |
| 5,327,906 A | 7/1994 | Fideler |
| 5,334,211 A | 8/1994 | Shiber |
| 5,342,293 A | 8/1994 | Zanger |
| 5,342,306 A | 8/1994 | Don Michael |
| 5,356,375 A | 10/1994 | Higley |
| 5,368,555 A | 11/1994 | Sussman et al. |
| 5,370,609 A | 12/1994 | Drasler et al. |
| 5,385,562 A | 1/1995 | Adams et al. |
| 5,389,072 A | 2/1995 | Imran |
| 5,392,778 A | 2/1995 | Horzewski |
| 5,395,315 A | 3/1995 | Griep |
| 5,403,274 A | 4/1995 | Cannon |
| 5,403,276 A | 4/1995 | Schechter et al. |
| 5,413,561 A | 5/1995 | Fischell et al. |
| 5,419,772 A | 5/1995 | Teitz et al. |
| 5,421,826 A | 6/1995 | Crocker et al. |
| 5,429,601 A | 7/1995 | Conley et al. |
| 5,443,078 A | 8/1995 | Uflacker |
| 5,443,443 A | 8/1995 | Shiber |

(56) References Cited

U.S. PATENT DOCUMENTS

| | | |
|---|---|---|
| 5,476,450 A | 12/1995 | Ruggio |
| 5,478,331 A | 12/1995 | Heflin et al. |
| 5,486,183 A | 1/1996 | Middleman et al. |
| 5,490,837 A | 2/1996 | Blaeser et al. |
| 5,496,267 A | 3/1996 | Drasler et al. |
| 5,507,738 A | 4/1996 | Ciervo |
| 5,524,180 A | 6/1996 | Wang et al. |
| 5,524,635 A | 6/1996 | Uflacker et al. |
| 5,527,274 A | 6/1996 | Zakko |
| 5,536,242 A | 7/1996 | Willard et al. |
| 5,538,002 A | 7/1996 | Boussignac et al. |
| 5,562,692 A | 10/1996 | Bair |
| 5,569,275 A | 10/1996 | Kotula et al. |
| 5,577,674 A | 11/1996 | Altonji |
| 5,605,545 A | 2/1997 | Nowosielski et al. |
| 5,606,968 A | 3/1997 | Mang |
| 5,624,394 A | 4/1997 | Barnitz et al. |
| 5,626,563 A | 5/1997 | Dodge et al. |
| 5,634,475 A | 6/1997 | Wolvek |
| 5,647,847 A | 7/1997 | Lafontaine et al. |
| 5,653,696 A | 8/1997 | Shiber |
| 5,660,180 A | 8/1997 | Malinowski et al. |
| 5,669,876 A | 9/1997 | Schechter et al. |
| 5,695,507 A | 12/1997 | Auth et al. |
| 5,709,661 A | 1/1998 | Van et al. |
| 5,713,849 A | 2/1998 | Bosma et al. |
| 5,713,851 A | 2/1998 | Boudewijn et al. |
| 5,713,878 A | 2/1998 | Moutafis et al. |
| 5,730,717 A | 3/1998 | Gelbfish |
| 5,735,535 A | 4/1998 | McCombs et al. |
| 5,766,191 A | 6/1998 | Trerotola |
| 5,772,674 A | 6/1998 | Nakhjavan |
| 5,785,685 A | 7/1998 | Kugler et al. |
| 5,795,322 A | 8/1998 | Boudewijn |
| 5,795,332 A | 8/1998 | Lucas et al. |
| 5,810,770 A | 9/1998 | Chin et al. |
| 5,827,229 A | 10/1998 | Auth et al. |
| 5,827,243 A | 10/1998 | Palestrant |
| 5,833,644 A | 11/1998 | Zadno-Azizi et al. |
| 5,843,022 A | 12/1998 | Willard et al. |
| 5,843,051 A | 12/1998 | Adams et al. |
| 5,853,384 A | 12/1998 | Bair |
| 5,855,567 A | 1/1999 | Reesemann |
| 5,868,702 A | 2/1999 | Stevens et al. |
| 5,871,462 A | 2/1999 | Yoder et al. |
| 5,876,414 A | 3/1999 | Straub |
| 5,885,238 A | 3/1999 | Stevens et al. |
| 5,885,244 A | 3/1999 | Leone et al. |
| 5,893,857 A | 4/1999 | Shturman et al. |
| 5,895,398 A | 4/1999 | Wensel et al. |
| 5,895,399 A | 4/1999 | Barbut et al. |
| 5,908,395 A | 6/1999 | Stalker et al. |
| 5,910,252 A | 6/1999 | Truitt et al. |
| 5,911,722 A | 6/1999 | Adler et al. |
| 5,916,192 A | 6/1999 | Nita et al. |
| 5,921,958 A | 7/1999 | Ressemann et al. |
| 5,938,645 A | 8/1999 | Gordon |
| 5,941,871 A | 8/1999 | Adams et al. |
| 5,944,686 A | 8/1999 | Patterson et al. |
| 5,957,901 A | 9/1999 | Mottola et al. |
| 5,989,210 A | 11/1999 | Morris et al. |
| 5,989,271 A | 11/1999 | Bonnette et al. |
| 6,001,112 A | 12/1999 | Taylor |
| 6,007,513 A | 12/1999 | Anis et al. |
| 6,019,728 A | 2/2000 | Iwata et al. |
| 6,022,336 A | 2/2000 | Zadno-Azizi et al. |
| 6,027,460 A | 2/2000 | Shturman |
| 6,080,170 A | 6/2000 | Nash et al. |
| 6,090,118 A | 7/2000 | McGuckin, Jr. |
| 6,096,001 A | 8/2000 | Drasler et al. |
| 6,126,635 A | 10/2000 | Simpson et al. |
| 6,129,697 A | 10/2000 | Drasler et al. |
| 6,129,698 A | 10/2000 | Beck |
| 6,146,355 A | 11/2000 | Biggs |
| 6,146,396 A | 11/2000 | Konya et al. |
| 6,152,909 A | 11/2000 | Bagaoisan et al. |
| 6,156,046 A | 12/2000 | Passafaro et al. |
| 6,159,230 A | 12/2000 | Samuels |
| 6,165,188 A | 12/2000 | Saadat et al. |
| 6,176,844 B1 | 1/2001 | Lee |
| 6,179,809 B1 | 1/2001 | Khairkhahan et al. |
| 6,179,851 B1 | 1/2001 | Barbut et al. |
| 6,183,432 B1 | 2/2001 | Milo |
| 6,190,357 B1 | 2/2001 | Ferrari et al. |
| 6,196,989 B1 | 3/2001 | Padget et al. |
| 6,206,898 B1 | 3/2001 | Honeycutt et al. |
| 6,216,573 B1 | 4/2001 | Moutafis et al. |
| 6,224,570 B1 | 5/2001 | Le et al. |
| 6,238,405 B1 | 5/2001 | Findlay et al. |
| 6,258,061 B1 | 7/2001 | Drasler et al. |
| 6,283,719 B1 | 9/2001 | Frantz et al. |
| 6,293,960 B1 | 9/2001 | Ken |
| 6,331,171 B1 | 12/2001 | Cohen |
| 6,348,040 B1 | 2/2002 | Stalker et al. |
| 6,375,635 B1 | 4/2002 | Moutafis et al. |
| 6,423,032 B2 | 7/2002 | Parodi |
| 6,440,148 B1 | 8/2002 | Shiber |
| 6,454,741 B1 | 9/2002 | Muni et al. |
| 6,454,775 B1 | 9/2002 | Demarais et al. |
| 6,471,683 B2 | 10/2002 | Drasler et al. |
| 6,481,439 B1 | 11/2002 | Lewis et al. |
| 6,488,672 B1 | 12/2002 | Dance et al. |
| 6,508,823 B1 | 1/2003 | Gonon |
| 6,533,772 B1 | 3/2003 | Sherts et al. |
| 6,544,209 B1 | 4/2003 | Drasler et al. |
| 6,544,231 B1 | 4/2003 | Palmer et al. |
| 6,551,302 B1 | 4/2003 | Rosinko et al. |
| 6,554,794 B1 | 4/2003 | Mueller et al. |
| 6,554,799 B1 | 4/2003 | Hatamura et al. |
| 6,558,366 B1 | 5/2003 | Drasler et al. |
| 6,558,401 B1 | 5/2003 | Azizi |
| 6,569,147 B1 | 5/2003 | Evans et al. |
| 6,569,148 B2 | 5/2003 | Bagaoisan et al. |
| 6,572,578 B1 | 6/2003 | Blanchard |
| 6,579,270 B2 | 6/2003 | Sussman et al. |
| 6,585,705 B1 | 7/2003 | Maginot et al. |
| 6,599,271 B1 | 7/2003 | Easley |
| 6,615,835 B1 | 9/2003 | Cise et al. |
| 6,616,679 B1 | 9/2003 | Khosravi et al. |
| 6,622,367 B1 | 9/2003 | Bolduc et al. |
| 6,623,495 B2 | 9/2003 | Findlay et al. |
| 6,635,034 B1 | 10/2003 | Cosmescu |
| 6,635,070 B2 | 10/2003 | Leeflang et al. |
| 6,638,235 B2 | 10/2003 | Miller et al. |
| 6,652,546 B1 * | 11/2003 | Nash ............. A61B 17/320758 606/159 |
| 6,652,548 B2 | 11/2003 | Evans et al. |
| 6,663,613 B1 | 12/2003 | Evans et al. |
| 6,669,710 B2 | 12/2003 | Moutafis et al. |
| 6,676,637 B1 | 1/2004 | Bonnette et al. |
| 6,702,830 B1 | 3/2004 | Demarais et al. |
| 6,719,717 B1 | 4/2004 | Johnson et al. |
| 6,723,081 B1 | 4/2004 | Hektner |
| 6,726,675 B1 | 4/2004 | Beyar |
| 6,752,800 B1 | 6/2004 | Winston et al. |
| 6,755,803 B1 | 6/2004 | Le et al. |
| 6,755,812 B2 | 6/2004 | Peterson et al. |
| 6,790,215 B2 | 9/2004 | Findlay et al. |
| 6,805,684 B2 | 10/2004 | Bonnette et al. |
| 6,818,001 B2 | 11/2004 | Wulfman et al. |
| 6,824,545 B2 | 11/2004 | Sepetka et al. |
| 6,824,550 B1 | 11/2004 | Noriega et al. |
| 6,830,577 B2 | 12/2004 | Nash et al. |
| 6,875,193 B1 | 4/2005 | Bonnette et al. |
| 6,899,712 B2 | 5/2005 | Moutafis et al. |
| 6,926,726 B2 | 8/2005 | Drasler et al. |
| 6,929,633 B2 | 8/2005 | Evans et al. |
| 6,936,056 B2 | 8/2005 | Nash et al. |
| 6,945,977 B2 | 9/2005 | Demarais et al. |
| 6,958,059 B2 | 10/2005 | Zadno-Azizi |
| 6,984,239 B1 | 1/2006 | Drasler et al. |
| 6,986,778 B2 | 1/2006 | Zadno-Azizi |
| 6,991,625 B1 | 1/2006 | Gately et al. |
| 7,008,434 B2 | 3/2006 | Kurz et al. |

(56) References Cited

U.S. PATENT DOCUMENTS

| | | | |
|---|---|---|---|
| 7,044,958 | B2 | 5/2006 | Douk et al. |
| 7,108,704 | B2 | 9/2006 | Trerotola |
| 7,122,017 | B2 | 10/2006 | Moutafis et al. |
| 7,220,269 | B1 | 5/2007 | Ansel et al. |
| 7,232,452 | B2 | 6/2007 | Adams et al. |
| 7,374,560 | B2 | 5/2008 | Ressemann et al. |
| 7,431,711 | B2 | 10/2008 | Moutafis et al. |
| 7,479,147 | B2 | 1/2009 | Honeycutt et al. |
| 7,481,222 | B2 | 1/2009 | Reissmann |
| 7,588,033 | B2 | 9/2009 | Wondka |
| 7,591,816 | B2 | 9/2009 | Wang et al. |
| 7,604,612 | B2 | 10/2009 | Ressemann et al. |
| 7,615,042 | B2 | 11/2009 | Beyar et al. |
| 7,621,886 | B2 | 11/2009 | Burnett |
| 7,654,996 | B2 | 2/2010 | Lynn |
| 7,655,016 | B2 | 2/2010 | Demarais et al. |
| 7,666,161 | B2 | 2/2010 | Nash et al. |
| 7,699,804 | B2 | 4/2010 | Barry et al. |
| 7,713,235 | B2 | 5/2010 | Torrance et al. |
| 7,717,685 | B2 | 5/2010 | Moutafis et al. |
| 7,717,898 | B2 | 5/2010 | Gately et al. |
| 7,736,355 | B2 | 6/2010 | Itou et al. |
| 7,753,868 | B2 | 7/2010 | Hoffa |
| 7,753,880 | B2 | 7/2010 | Malackowski |
| 7,766,894 | B2 | 8/2010 | Weitzner et al. |
| 7,776,005 | B2 | 8/2010 | Haggstrom et al. |
| 7,798,996 | B1 | 9/2010 | Haddad et al. |
| 7,798,999 | B2 | 9/2010 | Bailey et al. |
| 7,806,864 | B2 | 10/2010 | Haddad et al. |
| 7,833,239 | B2 | 11/2010 | Nash |
| 7,842,055 | B2 | 11/2010 | Pintor et al. |
| 7,846,175 | B2 | 12/2010 | Bonnette et al. |
| 7,862,575 | B2 | 1/2011 | Tal |
| 7,867,192 | B2 | 1/2011 | Bowman et al. |
| 7,875,004 | B2 | 1/2011 | Yodfat et al. |
| 7,879,022 | B2 | 2/2011 | Bonnette et al. |
| 7,887,510 | B2 | 2/2011 | Karpowicz et al. |
| 7,905,710 | B2 | 3/2011 | Wang et al. |
| 7,909,801 | B2 | 3/2011 | Hinchliffe |
| 7,909,810 | B2 | 3/2011 | Noone |
| 7,914,482 | B2 | 3/2011 | Urich et al. |
| 7,914,549 | B2 | 3/2011 | Morsi |
| 7,918,654 | B2 | 4/2011 | Adahan |
| 7,918,822 | B2 | 4/2011 | Kumar et al. |
| 7,918,835 | B2 | 4/2011 | Callahan et al. |
| 7,935,077 | B2 | 5/2011 | Thor et al. |
| 7,951,073 | B2 | 5/2011 | Freed |
| 7,951,107 | B2 | 5/2011 | Staid et al. |
| 7,951,112 | B2 | 5/2011 | Patzer |
| 7,959,603 | B2 | 6/2011 | Wahr et al. |
| 7,959,608 | B2 | 6/2011 | Nash et al. |
| 7,976,528 | B2 | 7/2011 | Nash et al. |
| 7,981,128 | B2 | 7/2011 | To et al. |
| 7,981,129 | B2 | 7/2011 | Nash et al. |
| 7,998,114 | B2 | 8/2011 | Lombardi |
| 8,007,490 | B2 | 8/2011 | Schaeffer et al. |
| 8,012,766 | B2 | 9/2011 | Graham |
| 8,021,351 | B2 | 9/2011 | Boldenow et al. |
| 8,034,018 | B2 | 10/2011 | Lutwyche |
| 8,043,312 | B2 | 10/2011 | Noriega et al. |
| 8,043,313 | B2 | 10/2011 | Krolik et al. |
| 8,062,246 | B2 | 11/2011 | Moutafis et al. |
| 8,062,257 | B2 | 11/2011 | Moberg et al. |
| 8,065,096 | B2 | 11/2011 | Moberg et al. |
| 8,066,677 | B2 | 11/2011 | Lunn et al. |
| 8,070,694 | B2 | 12/2011 | Galdonik et al. |
| 8,075,546 | B2 | 12/2011 | Carlisle et al. |
| 8,092,483 | B2 | 1/2012 | Galdonik et al. |
| 8,123,777 | B2 | 2/2012 | Krolik et al. |
| 8,140,146 | B2 | 3/2012 | Kim et al. |
| 8,142,458 | B2 | 3/2012 | Shturman |
| 8,152,782 | B2 | 4/2012 | Jang et al. |
| 8,152,951 | B2 | 4/2012 | Zawacki et al. |
| 8,157,787 | B2 | 4/2012 | Nash et al. |
| 8,162,877 | B2 | 4/2012 | Bonnette et al. |
| 8,162,966 | B2 | 4/2012 | Connor et al. |
| 8,177,739 | B2 | 5/2012 | Cartledge et al. |
| 8,182,462 | B2 | 5/2012 | Istoc et al. |
| 8,187,228 | B2 | 5/2012 | Bikovsky |
| 8,187,229 | B2 | 5/2012 | Weitzner et al. |
| 8,202,243 | B2 | 6/2012 | Morgan |
| 8,209,060 | B2 | 6/2012 | Ledford |
| 8,221,348 | B2 | 7/2012 | Hackett et al. |
| 8,226,673 | B2 | 7/2012 | Nash et al. |
| 8,246,573 | B2 | 8/2012 | Ali et al. |
| 8,246,580 | B2 | 8/2012 | Hopkins et al. |
| 8,257,298 | B2 | 9/2012 | Hamboly |
| 8,257,343 | B2 | 9/2012 | Chan et al. |
| 8,262,645 | B2 | 9/2012 | Bagwell et al. |
| 8,267,893 | B2 | 9/2012 | Moberg et al. |
| 8,287,485 | B2 | 10/2012 | Kimura et al. |
| 8,291,337 | B2 | 10/2012 | Gannin et al. |
| 8,292,841 | B2 | 10/2012 | Gregersen |
| 8,308,745 | B2 | 11/2012 | Seto et al. |
| 8,317,739 | B2 | 11/2012 | Kueebler |
| 8,317,770 | B2 | 11/2012 | Miesel et al. |
| 8,317,773 | B2 | 11/2012 | Appling et al. |
| 8,317,786 | B2 | 11/2012 | Dahla et al. |
| 8,323,239 | B2 | 12/2012 | Bednarek et al. |
| 8,323,268 | B2 | 12/2012 | Ring et al. |
| 8,337,175 | B2 | 12/2012 | Dion et al. |
| 8,337,451 | B2 | 12/2012 | Lareau et al. |
| 8,343,097 | B2 | 1/2013 | Pile-Spellman et al. |
| 8,343,131 | B2 | 1/2013 | Vinten-Johansen |
| 8,348,896 | B2 | 1/2013 | Wagner |
| 8,353,858 | B2 | 1/2013 | Kozak et al. |
| 8,353,860 | B2 | 1/2013 | Boulais et al. |
| 8,357,138 | B2 | 1/2013 | Pierpont et al. |
| 8,372,038 | B2 | 2/2013 | Urich et al. |
| 8,394,078 | B2 | 3/2013 | Torrance et al. |
| 8,398,579 | B2 | 3/2013 | Morris et al. |
| 8,398,581 | B2 | 3/2013 | Panotopoulos |
| 8,398,582 | B2 | 3/2013 | Gordon et al. |
| 8,414,521 | B2 | 4/2013 | Baker et al. |
| 8,414,522 | B2 | 4/2013 | Kamen et al. |
| 8,414,943 | B2 | 4/2013 | Wijngaarden et al. |
| 8,419,709 | B2 | 4/2013 | Haddad et al. |
| 8,425,458 | B2 | 4/2013 | Scopton |
| 8,430,837 | B2 | 4/2013 | Jenson et al. |
| 8,430,845 | B2 | 4/2013 | Wahr et al. |
| 8,430,861 | B2 | 4/2013 | Schwartz et al. |
| 8,439,876 | B2 | 5/2013 | Spohn et al. |
| 8,454,557 | B1 | 6/2013 | Qi et al. |
| 8,465,456 | B2 | 6/2013 | Stivland |
| 8,465,867 | B2 | 6/2013 | Kim |
| 8,483,980 | B2 | 7/2013 | Moberg et al. |
| 8,491,523 | B2 | 7/2013 | Thor et al. |
| 8,500,697 | B2 | 8/2013 | Kurth et al. |
| 8,506,537 | B2 | 8/2013 | Torstensen et al. |
| 8,523,801 | B2 | 9/2013 | Nash et al. |
| 8,529,498 | B2 | 9/2013 | Moutafis et al. |
| 8,545,432 | B2 | 10/2013 | Renati et al. |
| 8,545,514 | B2 | 10/2013 | Ferrera |
| 8,562,555 | B2 | 10/2013 | MacMahon et al. |
| 8,579,926 | B2 | 11/2013 | Pintor et al. |
| 8,597,238 | B2 | 12/2013 | Bonnette et al. |
| 8,608,699 | B2 | 12/2013 | Blomquist |
| 8,613,618 | B2 | 12/2013 | Brokx |
| 8,613,724 | B2 | 12/2013 | Lanier et al. |
| 8,617,110 | B2 | 12/2013 | Moberg et al. |
| 8,617,127 | B2 | 12/2013 | Woolston et al. |
| 8,623,039 | B2 | 1/2014 | Seto et al. |
| 8,628,549 | B2 | 1/2014 | To et al. |
| 8,641,671 | B2 | 2/2014 | Michaud et al. |
| 8,647,294 | B2 | 2/2014 | Bonnette et al. |
| 8,652,086 | B2 | 2/2014 | Gerg et al. |
| 8,657,777 | B2 | 2/2014 | Kozak et al. |
| 8,657,785 | B2 | 2/2014 | Torrance et al. |
| 8,663,259 | B2 | 3/2014 | Levine et al. |
| 8,668,464 | B2 | 3/2014 | Kensy et al. |
| 8,668,665 | B2 | 3/2014 | Gerg et al. |
| 8,670,836 | B2 | 3/2014 | Aeschlimann et al. |
| 8,672,876 | B2 | 3/2014 | Jacobson et al. |
| 8,681,010 | B2 | 3/2014 | Moberg et al. |

(56) References Cited

U.S. PATENT DOCUMENTS

| | | |
|---|---|---|
| 8,715,237 B2 | 5/2014 | Moberg et al. |
| 8,721,674 B2 | 5/2014 | Kusleika |
| 8,758,325 B2 | 6/2014 | Webster et al. |
| 8,758,364 B2 | 6/2014 | Eckhouse et al. |
| 8,783,151 B1 | 7/2014 | Janardhan et al. |
| 8,803,030 B1 | 8/2014 | Janardhan et al. |
| 8,814,892 B2 | 8/2014 | Galdonik et al. |
| 8,851,866 B2 | 10/2014 | Moutafis et al. |
| 8,852,219 B2 | 10/2014 | Wulfman et al. |
| 8,864,792 B2 | 10/2014 | Eckhouse et al. |
| 8,888,801 B2 | 11/2014 | To et al. |
| 8,900,179 B2 | 12/2014 | Jenson et al. |
| 8,900,214 B2 | 12/2014 | Nance et al. |
| 8,920,402 B2 | 12/2014 | Nash et al. |
| 8,932,320 B1 | 1/2015 | Janardhan et al. |
| 8,932,321 B1 | 1/2015 | Janardhan et al. |
| 8,936,447 B2 | 1/2015 | Abal |
| 8,945,030 B2 | 2/2015 | Weston |
| 8,962,561 B2 | 2/2015 | Shalgi et al. |
| 8,970,384 B2 | 3/2015 | Yodfat et al. |
| 8,974,418 B2 | 3/2015 | Bonnette et al. |
| 8,979,798 B2 | 3/2015 | Shener et al. |
| 8,986,241 B2 | 3/2015 | Evans et al. |
| 8,986,252 B2 | 3/2015 | Cummings et al. |
| 8,998,843 B2 | 4/2015 | Bonnette et al. |
| 9,005,237 B2 | 4/2015 | Eckhouse et al. |
| 9,011,114 B2 | 4/2015 | Farrell et al. |
| 9,017,294 B2 | 4/2015 | McGuckin et al. |
| 9,023,070 B2 | 5/2015 | Levine et al. |
| 9,024,768 B2 | 5/2015 | Mandro et al. |
| 9,033,925 B2 | 5/2015 | Moberg et al. |
| 9,034,008 B2 | 5/2015 | Eckhouse et al. |
| 9,042,938 B2 | 5/2015 | Nimbalker et al. |
| 9,078,691 B2 | 7/2015 | Morris et al. |
| 9,113,955 B2 | 8/2015 | Noriega et al. |
| 9,119,941 B2 | 9/2015 | Rollins et al. |
| 9,119,942 B1 | 9/2015 | Rollins et al. |
| 9,198,679 B2 | 12/2015 | To et al. |
| 9,238,122 B2 | 1/2016 | Mahli et al. |
| 9,248,221 B2 | 2/2016 | Look et al. |
| 9,254,144 B2 | 2/2016 | Nguyen et al. |
| 9,278,189 B2 * | 3/2016 | Corbett .............. A61M 60/857 |
| 9,282,992 B2 | 3/2016 | Levine et al. |
| 9,283,040 B2 | 3/2016 | Hendrick et al. |
| 9,308,016 B2 | 4/2016 | Escudero et al. |
| 9,314,263 B2 | 4/2016 | Escudero et al. |
| 9,332,999 B2 | 5/2016 | Ray et al. |
| 9,333,007 B2 | 5/2016 | Escudero et al. |
| 9,358,035 B2 | 6/2016 | Kojima |
| 9,402,938 B2 | 8/2016 | Aklog et al. |
| 9,433,427 B2 | 9/2016 | Look |
| 9,456,872 B2 | 10/2016 | Hendrick et al. |
| 9,474,543 B2 | 10/2016 | McGuckin et al. |
| 9,492,192 B2 | 11/2016 | To et al. |
| 9,492,193 B2 | 11/2016 | To et al. |
| 9,510,854 B2 | 12/2016 | Mallaby |
| 9,586,023 B2 | 3/2017 | Bonnette et al. |
| 9,592,073 B2 | 3/2017 | Kojima et al. |
| 9,597,480 B2 | 3/2017 | Purdy et al. |
| 9,693,789 B2 | 7/2017 | Garrison et al. |
| 9,700,346 B2 | 7/2017 | Levine et al. |
| 9,770,551 B1 | 9/2017 | Faden |
| 9,782,195 B2 | 10/2017 | Mactaggart et al. |
| 9,795,406 B2 | 10/2017 | Levine et al. |
| 9,808,266 B2 | 11/2017 | Ray et al. |
| 9,827,404 B2 | 11/2017 | Nance et al. |
| 9,833,257 B2 | 12/2017 | Bonnette et al. |
| 9,883,877 B2 | 2/2018 | Look et al. |
| 10,238,853 B2 | 3/2019 | Kume et al. |
| 10,314,608 B2 | 6/2019 | Jenson et al. |
| 10,383,983 B2 | 8/2019 | Aklog et al. |
| 10,390,926 B2 | 8/2019 | Janardhan et al. |
| 10,426,885 B2 | 10/2019 | Criado et al. |
| 10,499,944 B2 | 12/2019 | Mallaby |
| 10,531,883 B1 | 1/2020 | Deville et al. |
| 10,702,292 B2 | 7/2020 | Look et al. |
| 10,716,880 B2 | 7/2020 | Culbert et al. |
| 2001/0004700 A1 | 6/2001 | Honeycutt et al. |
| 2001/0051811 A1 | 12/2001 | Bonnette et al. |
| 2002/0016564 A1 | 2/2002 | Courtney et al. |
| 2002/0029052 A1 | 3/2002 | Evans et al. |
| 2002/0058904 A1 | 5/2002 | Boock et al. |
| 2002/0068895 A1 | 6/2002 | Beck |
| 2002/0133114 A1 | 9/2002 | Itoh et al. |
| 2002/0138095 A1 | 9/2002 | Mazzocchi et al. |
| 2002/0165575 A1 | 11/2002 | Saleh |
| 2002/0173819 A1 | 11/2002 | Leeflang et al. |
| 2002/0176788 A1 | 11/2002 | Moutafis et al. |
| 2002/0177789 A1 | 11/2002 | Ferry et al. |
| 2003/0032918 A1 | 2/2003 | Quinn |
| 2003/0040694 A1 | 2/2003 | Dorros et al. |
| 2003/0055404 A1 | 3/2003 | Moutafis |
| 2003/0069549 A1 | 4/2003 | MacMahon et al. |
| 2003/0083681 A1 | 5/2003 | Moutafis et al. |
| 2003/0088187 A1 | 5/2003 | Saadat et al. |
| 2003/0088209 A1 | 5/2003 | Chiu et al. |
| 2003/0139751 A1 | 7/2003 | Evans et al. |
| 2003/0144688 A1 | 7/2003 | Brady et al. |
| 2003/0216760 A1 | 11/2003 | Welch et al. |
| 2003/0220556 A1 | 11/2003 | Porat et al. |
| 2003/0236533 A1 | 12/2003 | Wilson et al. |
| 2004/0030281 A1 | 2/2004 | Goble et al. |
| 2004/0049149 A1 | 3/2004 | Drasler et al. |
| 2004/0049225 A1 | 3/2004 | Denison |
| 2004/0054322 A1 | 3/2004 | Vargas |
| 2004/0082915 A1 | 4/2004 | Kadan |
| 2004/0087988 A1 | 5/2004 | Heitzmann et al. |
| 2004/0097829 A1 | 5/2004 | McRury et al. |
| 2004/0143225 A1 * | 7/2004 | Callan .................. A61M 39/22 |
| | | 604/247 |
| 2004/0147871 A1 | 7/2004 | Burnett |
| 2004/0153109 A1 | 8/2004 | Tiedtke et al. |
| 2004/0158136 A1 | 8/2004 | Gough et al. |
| 2004/0167463 A1 | 8/2004 | Zawacki et al. |
| 2004/0193046 A1 | 9/2004 | Nash et al. |
| 2004/0199201 A1 | 10/2004 | Kellett et al. |
| 2004/0215222 A1 | 10/2004 | krivoruchko |
| 2004/0236214 A1 | 11/2004 | Opie et al. |
| 2004/0243157 A1 | 12/2004 | Connor et al. |
| 2005/0004594 A1 | 1/2005 | Nool et al. |
| 2005/0043682 A1 | 2/2005 | Kucklick et al. |
| 2005/0049547 A1 | 3/2005 | Anspach et al. |
| 2005/0065426 A1 | 3/2005 | Porat |
| 2005/0085769 A1 | 4/2005 | MacMahon et al. |
| 2005/0102165 A1 | 5/2005 | Oshita et al. |
| 2005/0159716 A1 | 7/2005 | Kobayashi et al. |
| 2005/0196748 A1 | 9/2005 | Ericson |
| 2005/0238503 A1 | 10/2005 | Rush et al. |
| 2005/0240116 A1 | 10/2005 | Saadat et al. |
| 2005/0240120 A1 | 10/2005 | Modesitt |
| 2005/0240146 A1 | 10/2005 | Nash et al. |
| 2005/0244521 A1 | 11/2005 | Strickland et al. |
| 2005/0277851 A1 | 12/2005 | Whittaker et al. |
| 2005/0283150 A1 | 12/2005 | Moutafis et al. |
| 2006/0009785 A1 | 1/2006 | Maitland et al. |
| 2006/0041245 A1 | 2/2006 | Ferry et al. |
| 2006/0058836 A1 | 3/2006 | Bose et al. |
| 2006/0063973 A1 | 3/2006 | Makower et al. |
| 2006/0064051 A1 | 3/2006 | Gross |
| 2006/0064123 A1 | 3/2006 | Bonnette et al. |
| 2006/0074442 A1 | 4/2006 | Noriega et al. |
| 2006/0093989 A1 | 5/2006 | Hahn et al. |
| 2006/0142630 A1 | 6/2006 | Meretei |
| 2006/0149191 A1 | 7/2006 | DiFiore |
| 2006/0184186 A1 | 8/2006 | Noone |
| 2006/0212055 A1 | 9/2006 | Karabey et al. |
| 2006/0229550 A1 | 10/2006 | Staid et al. |
| 2006/0229587 A1 | 10/2006 | Beyar et al. |
| 2006/0264808 A1 | 11/2006 | Staid et al. |
| 2006/0282150 A1 | 12/2006 | Olson et al. |
| 2007/0016105 A1 | 1/2007 | Mamourian |
| 2007/0060879 A1 | 3/2007 | Weitzner et al. |
| 2007/0073233 A1 | 3/2007 | Thor et al. |
| 2007/0073268 A1 | 3/2007 | Goble et al. |

(56) References Cited

U.S. PATENT DOCUMENTS

| | | |
|---|---|---|
| 2007/0078438 A1 | 4/2007 | Okada |
| 2007/0118165 A1 | 5/2007 | Demello et al. |
| 2007/0135812 A1 | 6/2007 | Sartor |
| 2007/0167804 A1 | 7/2007 | Park et al. |
| 2007/0197956 A1 | 8/2007 | Le et al. |
| 2007/0197963 A1 | 8/2007 | Griffiths et al. |
| 2007/0219467 A1 | 9/2007 | Clark et al. |
| 2007/0225615 A1 | 9/2007 | Chechelski et al. |
| 2007/0225739 A1 | 9/2007 | Pintor et al. |
| 2007/0239182 A1 | 10/2007 | Glines et al. |
| 2007/0249990 A1 | 10/2007 | Cosmescu |
| 2007/0270755 A1 | 11/2007 | Von et al. |
| 2007/0299306 A1 | 12/2007 | Parasher et al. |
| 2008/0009784 A1 | 1/2008 | Leedle et al. |
| 2008/0091061 A1 | 4/2008 | Kumar et al. |
| 2008/0097339 A1 | 4/2008 | Ranchod et al. |
| 2008/0097465 A1 | 4/2008 | Rollins et al. |
| 2008/0097563 A1 | 4/2008 | Petrie et al. |
| 2008/0108960 A1 | 5/2008 | Shapland et al. |
| 2008/0119824 A1 | 5/2008 | Weitzner et al. |
| 2008/0125698 A1 | 5/2008 | Gerg et al. |
| 2008/0125798 A1 | 5/2008 | Osborne et al. |
| 2008/0195058 A1 | 8/2008 | Moutafis et al. |
| 2008/0195139 A1 | 8/2008 | Donald et al. |
| 2008/0243054 A1 | 10/2008 | Mollstam et al. |
| 2008/0243153 A1 | 10/2008 | Nguyen et al. |
| 2008/0249501 A1 | 10/2008 | Yamasaki |
| 2008/0255539 A1 | 10/2008 | Booth |
| 2008/0255596 A1 | 10/2008 | Jenson et al. |
| 2008/0294008 A1 | 11/2008 | Toyama |
| 2008/0294181 A1 | 11/2008 | Wensel et al. |
| 2008/0306465 A1 | 12/2008 | Bailey et al. |
| 2008/0319376 A1 | 12/2008 | Wilcox et al. |
| 2009/0018566 A1 | 1/2009 | Escudero et al. |
| 2009/0048607 A1 | 2/2009 | Rockley |
| 2009/0054825 A1 | 2/2009 | Melsheimer et al. |
| 2009/0082722 A1 | 3/2009 | Munger et al. |
| 2009/0105645 A1 | 4/2009 | Kidd et al. |
| 2009/0105690 A1 | 4/2009 | Schaeffer et al. |
| 2009/0157057 A1 | 6/2009 | Ferren et al. |
| 2009/0264940 A1 | 10/2009 | Beale et al. |
| 2009/0292212 A1 | 11/2009 | Ferren et al. |
| 2009/0306476 A1 | 12/2009 | Banik et al. |
| 2009/0306692 A1 | 12/2009 | Barrington et al. |
| 2010/0010524 A1 | 1/2010 | Barrington et al. |
| 2010/0030134 A1 | 2/2010 | Fitzgerald et al. |
| 2010/0030186 A1 | 2/2010 | Stivland |
| 2010/0094201 A1 | 4/2010 | Mallaby |
| 2010/0145302 A1 | 6/2010 | Cull et al. |
| 2010/0160851 A1 | 6/2010 | Dimalanta et al. |
| 2010/0174233 A1 | 7/2010 | Kuban et al. |
| 2010/0191178 A1 | 7/2010 | Ross et al. |
| 2010/0204613 A1 | 8/2010 | Rollins et al. |
| 2010/0204672 A1 | 8/2010 | Lockhart et al. |
| 2010/0217275 A1 | 8/2010 | Carmeli et al. |
| 2010/0217276 A1 | 8/2010 | Garrison et al. |
| 2010/0228273 A1 | 9/2010 | Staid et al. |
| 2010/0268236 A1 | 10/2010 | Moutafis et al. |
| 2010/0274191 A1 | 10/2010 | Ting |
| 2010/0280534 A1 | 11/2010 | Sher |
| 2011/0034986 A1 | 2/2011 | Chou et al. |
| 2011/0091331 A1 | 4/2011 | Moutafis et al. |
| 2011/0092892 A1 | 4/2011 | Nitsan et al. |
| 2011/0106019 A1 | 5/2011 | Bagwell et al. |
| 2011/0152920 A1 | 6/2011 | Eckhouse et al. |
| 2011/0160683 A1 | 6/2011 | Pinotti et al. |
| 2011/0282426 A1 | 11/2011 | Mitra et al. |
| 2012/0059340 A1 | 3/2012 | Larsson |
| 2012/0059354 A1 | 3/2012 | Zarate |
| 2012/0065656 A1 | 3/2012 | Karwei |
| 2012/0065660 A1 | 3/2012 | Ferrera et al. |
| 2012/0071907 A1 | 3/2012 | Pintor et al. |
| 2012/0078080 A1 | 3/2012 | Foley et al. |
| 2012/0123509 A1 | 5/2012 | Merrill et al. |
| 2012/0130415 A1 | 5/2012 | Tal et al. |
| 2012/0165756 A1 | 6/2012 | Root et al. |
| 2012/0239008 A1 | 9/2012 | Fojtik |
| 2012/0239064 A1 | 9/2012 | Cartier et al. |
| 2012/0239066 A1 | 9/2012 | Levine et al. |
| 2012/0259265 A1 | 10/2012 | Salehi et al. |
| 2012/0277665 A1 | 11/2012 | Tachoire et al. |
| 2012/0289910 A1 | 11/2012 | Shtul et al. |
| 2012/0291811 A1 | 11/2012 | Dabney et al. |
| 2012/0330196 A1 | 12/2012 | Nita |
| 2013/0085381 A1 | 4/2013 | Comerota et al. |
| 2013/0184734 A1 | 7/2013 | Morris et al. |
| 2013/0190701 A1 | 7/2013 | Kirn |
| 2013/0218186 A1 | 8/2013 | Dubois et al. |
| 2013/0245543 A1 | 9/2013 | Gerg et al. |
| 2013/0267891 A1 | 10/2013 | Malhi et al. |
| 2013/0281788 A1 | 10/2013 | Garrison |
| 2013/0310809 A1 | 11/2013 | Armstrong et al. |
| 2013/0310845 A1 | 11/2013 | Thor et al. |
| 2013/0331776 A1 | 12/2013 | Klein et al. |
| 2014/0005699 A1 | 1/2014 | Bonnette et al. |
| 2014/0058361 A1 | 2/2014 | Gordon |
| 2014/0142594 A1 | 5/2014 | Fojtik |
| 2014/0147246 A1 | 5/2014 | Chappel et al. |
| 2014/0148830 A1 | 5/2014 | Bowman |
| 2014/0155931 A1 | 6/2014 | Bose et al. |
| 2014/0228569 A1 | 8/2014 | Okumura et al. |
| 2014/0228869 A1 | 8/2014 | Bonnette et al. |
| 2014/0276920 A1 | 9/2014 | Hendrick et al. |
| 2014/0309589 A1 | 10/2014 | Momose et al. |
| 2014/0323906 A1 | 10/2014 | Peatfield et al. |
| 2014/0360494 A1 | 12/2014 | Herskovic |
| 2014/0378951 A1 | 12/2014 | Dye |
| 2015/0025446 A1 | 1/2015 | Jacobson et al. |
| 2015/0032138 A1 | 1/2015 | Jenson et al. |
| 2015/0094673 A1 | 4/2015 | Pratt et al. |
| 2015/0094748 A1 | 4/2015 | Nash et al. |
| 2015/0142030 A1 | 5/2015 | MacTaggart et al. |
| 2015/0257724 A1 | 9/2015 | Lautenschlager |
| 2015/0305765 A1 | 10/2015 | Fojtik et al. |
| 2015/0327875 A1 | 11/2015 | Look et al. |
| 2015/0374391 A1 | 12/2015 | Quick et al. |
| 2016/0051323 A1 | 2/2016 | Stigall et al. |
| 2016/0058614 A1 | 3/2016 | Ross et al. |
| 2016/0143721 A1 | 5/2016 | Rosenbluth et al. |
| 2016/0220741 A1 | 8/2016 | Garrison et al. |
| 2017/0065396 A1* | 3/2017 | Look .................. A61B 17/22 |
| 2017/0079672 A1 | 3/2017 | Quick |
| 2017/0105745 A1 | 4/2017 | Rosenbluth et al. |
| 2017/0172603 A1 | 6/2017 | Bonnette et al. |
| 2017/0181760 A1 | 6/2017 | Look et al. |
| 2017/0265885 A1 | 9/2017 | Bonnette et al. |
| 2017/0281204 A1 | 10/2017 | Garrison et al. |
| 2017/0290598 A1 | 10/2017 | Culbert et al. |
| 2018/0207397 A1 | 7/2018 | Look et al. |
| 2018/0214172 A1 | 8/2018 | Donnelly et al. |
| 2018/0338770 A1 | 11/2018 | Mogi et al. |
| 2020/0345904 A1 | 11/2020 | Casey et al. |
| 2020/0367917 A1 | 11/2020 | Teigen et al. |

FOREIGN PATENT DOCUMENTS

| | | |
|---|---|---|
| CN | 201603160 U | 10/2010 |
| CN | 103767760 A | 5/2014 |
| DE | 3715418 A1 | 11/1987 |
| DE | 4018736 A1 | 1/1992 |
| EP | 0709110 A1 | 5/1996 |
| EP | 0726466 A1 | 8/1996 |
| EP | 0806213 A1 | 11/1997 |
| EP | 1092396 A2 | 4/2001 |
| EP | 1488748 A1 | 12/2004 |
| EP | 2301450 A1 | 3/2011 |
| EP | 2859902 A1 | 4/2015 |
| EP | 2131759 B1 | 10/2017 |
| JP | 06-125915 A | 5/1994 |
| JP | 06-205784 A | 7/1994 |
| JP | 06-205785 A | 7/1994 |
| JP | 07-299078 A | 11/1995 |
| JP | 2001-161700 A | 6/2001 |
| JP | 2003010194 A | 1/2003 |

(56) References Cited

FOREIGN PATENT DOCUMENTS

| | | |
|---|---|---|
| JP | 2003-101194 A | 4/2003 |
| JP | 2003-514632 A | 4/2003 |
| JP | 2003260127 A | 9/2003 |
| JP | 2003-290236 A | 10/2003 |
| JP | 2004-514466 A | 5/2004 |
| JP | 2007-160109 A | 6/2007 |
| JP | 2009039216 A | 2/2009 |
| JP | 2013-154171 A | 8/2013 |
| JP | 2013-180156 A | 9/2013 |
| WO | WO1990-05493 | 5/1990 |
| WO | 96/01079 A1 | 1/1996 |
| WO | 96/35469 A1 | 11/1996 |
| WO | 99/01079 A1 | 1/1999 |
| WO | 99/18850 A1 | 4/1999 |
| WO | 00/69348 A1 | 11/2000 |
| WO | 01/37916 A1 | 5/2001 |
| WO | WO0219928 A2 | 3/2002 |
| WO | 02/26289 A1 | 4/2002 |
| WO | 2004/100772 A2 | 11/2004 |
| WO | 2005/004968 A1 | 1/2005 |
| WO | 2006/081238 A2 | 8/2006 |
| WO | 2007/087404 A2 | 8/2007 |
| WO | 2007/143633 A2 | 12/2007 |
| WO | 2008/097993 A2 | 8/2008 |
| WO | 2008/121481 A1 | 10/2008 |
| WO | 2010/023617 A1 | 3/2010 |
| WO | 2010/023671 A2 | 3/2010 |
| WO | 2015/179329 A1 | 11/2015 |
| WO | WO2016/126974 A1 | 8/2016 |
| WO | 2017/112922 A1 | 6/2017 |
| WO | 2018/215840 A1 | 11/2018 |

OTHER PUBLICATIONS

"Angiojet Ultra Power Pulse Kit Information for Use", Medrad, Inc., downloaded from internet Jan. 23, 2017.
CN201079629Y (Machine Translation, Sep. 7, 2018) (3 pages).
Comparison of Dimensions and Aspiration Rate of the Pronto V3, Pronto LP, Export XT, Export AP, Fetch, Xtract, Diver C.E, and QuickCat Catheter, Vascular Solutions, Inc., downloaded from internet Oct. 22, 2014.
Dalal, J., Sahoo, P., Dhall, A., Kapoor, R., Krishnamurthy, A., Shetty, S., Trivedi, S., Kahali, D., Shah, B., Chockalingam, K., Abdullakutty, J., Shetty, P., Chopra, A., Ray, R., Desai, D., Pachiyappan, Ratnaparkhi, G., Sharma, M., Sambasivam, K. "Role of thrombysis in reperfusion therapy for management of AMI: Indian scenario," Indian Heart Journal, 2013, pp. 566-585, vol. 63, Cardiological Society of India, Bombay, India.
Franetzki, M., "Confusion in the Terminology of Insulin Devices", Diabetes Care, Jan.-Feb. 1982, pp. 74-75, vol. 5, No. 1, American Diabetes Association, Alexandria, USA.
Frolich, G., Meier, P., White, S., Yellon, D., Hausenloy, D., "Myocardial reperfusion injury: looking beyond primary PCI", European Heart Journal Jun. 2013, pp. 1714-1722, vol. 34, No. 23, Elsevier, Amsterdam, The Netherlands.
Prasad, A., Stone, G., Holmes, D., Gersh, B., Peperfusion Injury, Microvascular Dysfunction, and Carioprotection: The "Dark Side" of Reperfusion, Circulation, Nov. 24, 2009, pp. 2105-2112, vol. 120, American Heart Association, Dallas, USA.
Principles and Practice of Pharmacology for Anaesthetists, ed. Calvey, T., Williams, N., 2008, pp. 324-327, 5th Edition, Blackwell Publishing, Malden, USA.
Puddu, P., Ianetta, L., Placanica, A., Cuturello, D., Schiariti, M., Manfrini, O., "The role of Glycoprotein llb/llla inhibitors in acute coronary syndromes and the interference with anemia," International Journal of Cardiology, 2016, pp. 1091-1096, vol. 222, Elsevier, Amsterdam, The Netherlands.
Rodriquez, R., Conde-Green, A., "Quantification of Negative Pressures Generated by Syringes of Different Calibers Used for Liposuction", Plastic & Reconstructive Surgery, Aug. 2012; pp. 383e-384e, vol. 130, No. 2, Lippicott Williams & Wilkins, Philadelphia, USA.

Saudek, C., Selam, J-L, Pitt, H., Waxman, K., Rubio, M., Jeandidier, N., Turner, D., Fischell, R., Charles, M., "A Preliminary trial of the Programmable Implantable Medication System for Insulin Delivery", The New England Journal of Medicine, Aug. 31, 1989, pp. 574-579, vol. 321, No. 9, Massachusetts Medical Society, Boston, USA.
Selam, J-L, "Development of Implantable Insulin Pumps: Long is the Road", Diabetic Medicine, Nov. 1988, pp. 724-733, vol. 5, No. 8, Wiley, Chichester, UK.
Stys, A., Stys, T., Rajpurohit, N., Khan, M. "A Novel Application of GuideLiner Catheter for Thrombectomy in Acute Myocardial Infarction: A Case Series", Journal of Invasive cardiology, Nov. 2013, pp. 620-624, vol. 25, No. 11, King of Prussia, USA.
Van De Werf, F, "The ideal fibrinolytic: can drug design improve clinical results?" European Heart Journal, 1999, pp. 1452-1458, vol. 20, Elsevier, Amsterdam, The Netherlands.
Warmerdam, P., Vanderlick, K., Vandervoort, P., de Smedt, H., Plaisance, S., De Maeyer, M., Collen, D. "Saphylokinase-Specific-Cell-Mediated Immunity in Humans," The Journal of Immunology, 2002, pp. 155-161, vol. 168, Williams & Wilkins Co., Baltimore, USA.
Extended European Search Report dated Aug. 31, 2018, in EP App. No. 16843162.5 filed Sep. 3, 2016 (10 pages).
PCT International Search Report and Written Opinion for PCT/US2016/050302, Applicant: Vesatek, LLC, Forms PCT/ISA/220, 210, and 237 dated Nov. 29, 2016 (10 pages).
Gousios, A, Shearn, M, "Effect of Intravenous Heparin on Human Blood Viscosity", Circulation, Dec. 1959, pp. 1063-1066, vol. 20, American Heart Association, Dallas, USA.
Harvard Health; Normal Body Temperature: Rethinking the normal human body temperature; p. 1; published Apr. 1, 2006; http://www.health.harvard.edu/press.sub.-releases/normal.sub.-body.sub.- -temperature.
Infusion Liquid Flow Sensors—Safe, Precise and Reliable, Sensirion, downloaded from Internet Apr. 3, 2015.
Irsigler, K, Kritz, H., Hagmuller, G., Franezki, M., Prestele, K, Thurow, H., Geisen, K., "Long-term Continuous Intraperitoneal Insulin Infusion with an Implanted Remote-Controlled Insulin Infusion Device", Diabetes, Dec. 1981, pp. 1072-1075, vol. 30, No. 12, American Diabetes Association, New York, USA.
JP2003260127A (Machine Translation, Sep. 7, 2018) (5 pages).
Kritz, H., Hagmuller, G, Lovett, R., Irsigler, K., "Implanted Constant Basal Rate Insulin Infusion Devices for Type 1 (Insulin-Dependent) Diabetic Patients", Diabetologia, Aug. 1983, pp. 78-81, vol. 25, No. 2, Springer-Veriag, Berlin, Germany.
Lipinski, M., Lee, R., Gaglia, M., Torguson, R., Garcia-Garda, H., Pichard, A., Satler, L., Waksman, R. "Comparison of heparin, bivalirudin, and different glycoprotein IIb/IIIa inhibitor regimens for anticoagulation during percutaneous coronary intervention: A network meta-analysis," Cardiovascular Revascularization Medicine, 2016, pp. 535-545, vol. 17, Elsevier, New York, USA.
Makes even the most difficult intervention a Fast and Smooth Run. GuideLiner brochure. Vascular Solutions,. Inc., downloaded from internet Apr. 9, 2015.
Micossi, P., Cristallo, M., Galiberti, G, Librenti, M., Petrella, G., Pozza, G., Hutter, R., Babic, D., Hagmuller, G., Vert, F., Irsigler, K., Walter, H., Ladik, T., Flaschentrager, T., Gunther, A., Kronski, K., Mehnert, H., Bauersachs, R., Ruhland, B., Piwernetz, K., Renner, R., Hepp, K., Buchholz, G., Kollert, D., Wohlers, C,, Jahrling, P., Franetzki, M., Pfeiffer, C., Neuhauser, C., Seipke. G., Deutschlander. N., Zoltobrocki, M., "One-Year Trial of a Remote-Controlled Implantable Insulin Infusion System in Type I Diabetic Patients", The Lancet, Oct. 15, 1988, pp. 866-869, vol. 2, No. 8616, Elsevier Ltd. , New York, USA.
Parikh, A., Ali, F., "Novel Use of GuideLiner Catheter to Perform Aspiration Thrombectomy in a Saphenous Vein Graft" Cath Lab Digest Oct. 2013, downloaded from internet Oct. 22, 2014.

(56) References Cited

OTHER PUBLICATIONS

Pechlaner, C., Knapp, E., Wiedermann, C. "Hypersensitivity reactions associated with recombinant tissue-type plasminogen activator and urokinase," Blood Coagulation and Fibrinolysis, 2001, pp. 491-494, vol. 12, Lippincott Williams & Wilkins, Hagerstown, USA.

* cited by examiner

_US 11,678,905 B2_

SYSTEMS AND METHODS FOR REMOVAL OF BLOOD AND THROMBOTIC MATERIAL

INCORPORATION BY REFERENCE TO ANY PRIORITY APPLICATIONS

This application claims the benefit of priority to U.S. Provisional Patent Application No. 62/700,763, filed on Jul. 19, 2018, which is herein incorporated by reference in its entirety for all purposes. Priority is claimed pursuant to 35 U.S.C. § 119.

BACKGROUND OF THE INVENTION

The present disclosure pertains generally to medical devices and methods of their use. More particularly, the present invention pertains to aspiration and thrombectomy devices and methods of use thereof.

DESCRIPTION OF THE RELATED ART

Several devices and systems already exist to aid in the removal of thrombotic material. These include simple aspiration tube type devices using vacuum syringes to extract thrombus into the syringe, simple flush-and-aspirate devices, more complex devices with rotating components the pull in, macerate and transport thrombotic material away from the distal tip using a mechanical auger, systems that use very high pressure to macerate the thrombus and create a venturi effect to flush the macerated material away.

SUMMARY OF THE INVENTION

In one embodiment of the present disclosure, a method for improving a flow condition through a catheter includes providing an aspiration catheter including an elongate shaft configured for placement within a blood vessel of a subject, a supply lumen and an aspiration lumen each extending along the shaft, the supply lumen having a proximal end and a distal end, and the aspiration lumen having a proximal end and an open distal end, and an opening at or near the distal end of the supply lumen, the opening configured to allow the injection of pressurized fluid from a first fluid source into the aspiration lumen at or near the distal end of the aspiration lumen when the pressurized fluid is caused or allowed to flow through the supply lumen, providing a sheath including a proximal end, a distal end and a lumen extending between the proximal end and the distal end, the lumen configured for placement of the aspiration catheter therethrough, the sheath further including an extension conduit in fluid communication with the lumen of the sheath and extending from the sheath, the extension conduit configured for coupling to a second fluid source, providing a seal associated with the proximal end of the sheath and configured to seal the lumen of the sheath around the elongate shaft of the aspiration catheter when the aspiration catheter is in place within the sheath, providing a tubing set including a first conduit having a distal end configured to couple to the aspiration lumen of the aspiration catheter and a proximal end configured to couple to a vacuum source, and a second conduit having a distal end configured to couple to the supply lumen of the aspiration catheter and a proximal end configured to couple to the first fluid source, wherein the tubing set is configured to couple to a pump configured to pressurize fluid from the first fluid source or allow pressurized fluid from the first fluid source to be transferred to the supply lumen, such that the pressurized fluid is capable of flowing through the supply lumen from the proximal end of the supply lumen to the distal end of the supply lumen, coupling the distal end of the first conduit of the tubing set to the aspiration lumen of the aspiration catheter, coupling the proximal end of the first conduit of the tubing set to the vacuum source, coupling the distal end of the second conduit to the supply lumen of the aspiration catheter, coupling the proximal end of the second conduit to the first fluid source, inserting the distal end of the sheath within the vasculature of a subject, placing the aspiration catheter through the sheath and advancing the aspiration catheter such that the open distal end of the aspiration lumen of the aspiration catheter is distal to the distal end of the sheath and is in proximity to a thrombus within a blood vessel of the subject, coupling the extension conduit to the second fluid source, and activating the pump such that pressurized fluid from the first fluid source is applied to the proximal end of the supply lumen of the aspiration catheter, wherein when sufficient flowable material is present adjacent the open distal end of the aspiration lumen, at least some of the flowable material is caused to flow through the aspiration lumen from the open distal end to the proximal end, and into an interior of the vacuum source, and when insufficient flowable material is present adjacent the open distal end of the aspiration lumen, fluid from the second fluid source is caused to flow through the lumen of the sheath from the proximal end to the distal end, and at least some of the fluid from the second fluid source is delivered into the blood vessel of the subject.

In another embodiment of the present disclosure, a method for identifying a no flow or low flow condition through a catheter includes providing an aspiration catheter including an elongate shaft configured for placement within a blood vessel of a subject, a supply lumen and an aspiration lumen each extending along the shaft, the supply lumen having a proximal end and a distal end, and the aspiration lumen having a proximal end and an open distal end, and an opening at or near the distal end of the supply lumen, the opening configured to allow the injection of pressurized fluid into the aspiration lumen at or near the distal end of the aspiration lumen when the pressurized fluid is caused or allowed to flow through the supply lumen, providing a sheath including a proximal end, a distal end and a lumen extending between the proximal end and the distal end, the lumen configured for placement of the aspiration catheter therethrough, the sheath further including an extension conduit in fluid communication with the lumen of the sheath and extending from the sheath, the extension conduit configured for coupling to a second fluid source, the extension conduit fluidly coupled to a valve having a first position configured to selectively couple the extension conduit to a fluid source containing a contrast agent and a second position configured to selectively couple the extension conduit to a fluid source containing substantially no contrast agent, providing a seal associated with the proximal end of the sheath and configured to seal the lumen of the sheath around the elongate shaft of the aspiration catheter when the aspiration catheter is in place within the sheath, providing a tubing set including a first conduit having a distal end configured to couple to the aspiration lumen of the aspiration catheter and a proximal end configured to couple to a vacuum source, and a second conduit having a distal end configured to couple to the supply lumen of the aspiration catheter and a proximal end configured to couple to a first fluid source, wherein the tubing set is configured to couple to a pressurization element configured to pressurize fluid from the first fluid source or allow pressurized fluid from the first fluid source to be transferred to the supply lumen, such that the pressurized fluid is capable of flowing through the supply lumen from the proximal end of the supply lumen to the distal end of the supply lumen, coupling the distal end of the first conduit of the tubing set to the aspiration lumen of the aspiration catheter, coupling the proximal end of the first conduit of the tubing set to the vacuum source, coupling the distal end of the second conduit to the supply lumen of the aspiration catheter, coupling the proximal end of the second conduit to the first fluid source, inserting the distal end of the sheath within the vasculature of a subject, placing the aspiration catheter through the sheath and advancing the aspiration catheter such that the open distal end of the aspiration lumen of the aspiration catheter is in proximity to a thrombus within a blood vessel of the subject, coupling the extension conduit to at least the fluid source containing a contrast agent, placing or maintaining the valve in the first position, and activating the pressurization element such that pressurized fluid from the first fluid source is applied to the proximal end of the supply lumen of the aspiration catheter, wherein when sufficient flowable material is present adjacent the open distal end of the aspiration lumen, at least some of the flowable material is caused to flow through the aspiration lumen from the open distal end to the proximal end, and into an interior of the vacuum source, and when insufficient flowable material is present adjacent the open distal end of the aspiration lumen, fluid from the fluid source containing a contrast agent is caused to flow through the lumen of the sheath between the proximal end and the distal end, and at least some of the fluid from the fluid source containing a contrast agent is delivered into the blood vessel of the subject.

In yet another embodiment of the present disclosure, a method for identifying a no flow or low flow condition through a catheter includes providing an aspiration catheter including an elongate shaft configured for placement within a blood vessel of a subject, a supply lumen and an aspiration lumen each extending along the shaft, the supply lumen having a proximal end and a distal end, and the aspiration lumen having a proximal end and an open distal end, and an opening at or near the distal end of the supply lumen, the opening configured to allow the injection of pressurized fluid into the aspiration lumen at or near the distal end of the aspiration lumen when the pressurized fluid is caused or allowed to flow through the supply lumen, providing a sheath including a proximal end, a distal end and a lumen extending between the proximal end and the distal end, the lumen configured for placement of the aspiration catheter therethrough, the sheath further including an extension conduit in fluid communication with the lumen of the sheath and extending from the sheath, the extension conduit configured for coupling to a second fluid source, the second fluid source containing a contrast agent, providing a seal associated with the proximal end of the sheath and configured to seal the lumen of the sheath around the elongate shaft of the aspiration catheter when the aspiration catheter is in place within the sheath, providing a tubing set including a first conduit having a distal end configured to couple to the aspiration lumen of the aspiration catheter and a proximal end configured to couple to a vacuum source, and a second conduit having a distal end configured to couple to the supply lumen of the aspiration catheter and a proximal end configured to couple to a first fluid source, wherein the tubing set is configured to couple to a pressurization element configured to pressurize fluid from the first fluid source or allow pressurized fluid from the first fluid source to be transferred to the supply lumen, such that the pressurized fluid is capable of flowing through the supply lumen from the proximal end of the supply lumen to the distal end of the supply lumen, coupling the distal end of the first conduit of the tubing set to the aspiration lumen of the aspiration catheter, coupling the proximal end of the first conduit of the tubing set to the vacuum source, coupling the distal end of the second conduit to the supply lumen of the aspiration catheter, coupling the proximal end of the second conduit to the first fluid source, inserting the distal end of the sheath within the vasculature of a subject, placing the aspiration catheter through the sheath and advancing the aspiration catheter such that the open distal end of the aspiration lumen of the aspiration catheter is in proximity to a thrombus within a blood vessel of the subject, coupling the extension conduit to at least the fluid source containing a contrast agent, and activating the pressurization element such that pressurized fluid from the first fluid source is applied to the proximal end of the supply lumen of the aspiration catheter, wherein when sufficient flowable material is present adjacent the open distal end of the aspiration lumen, at least some of the flowable material is caused to flow through the aspiration lumen from the open distal end to the proximal end, and into an interior of the vacuum source, and when insufficient flowable material is present adjacent the open distal end of the aspiration lumen, fluid from the fluid source containing a contrast agent is caused to flow through the lumen of the sheath between the proximal end and the distal end, and at least some of the fluid from the fluid source containing a contrast agent is delivered into the blood vessel of the subject.

In still another embodiment of the present disclosure, a system for aspirating thrombus includes an aspiration catheter including an elongate shaft configured for placement within a blood vessel of a subject, a supply lumen and an aspiration lumen each extending along the shaft, the supply lumen having a proximal end and a distal end, and the aspiration lumen having a proximal end and an open distal end, and an opening at or near the distal end of the supply lumen, the opening configured to allow the injection of pressurized fluid into the aspiration lumen at or near the distal end of the aspiration lumen when the pressurized fluid is caused or allowed to flow through the supply lumen, a tubing set including a first conduit having a distal end configured to couple to the aspiration lumen of the aspiration catheter and a proximal end configured to couple to a vacuum source, and a second conduit having a distal end configured to couple to the supply lumen of the aspiration catheter and a proximal end configured to couple to a first fluid source, a pressurization element configured to couple to the tubing set and further configured to pressurize fluid from the first fluid source or allow pressurized fluid from the first fluid source to be transferred to the supply lumen, such that the pressurized fluid is capable of flowing through the supply lumen from the proximal end of the supply lumen to the distal end of the supply lumen, a sheath having a proximal end, a distal end and a lumen extending between the proximal end and the distal end, the lumen configured for placement of the aspiration catheter therethrough, the sheath further including an extension conduit in fluid communication with the lumen of the sheath and extending from the sheath, the extension conduit configured for coupling to a second fluid source, a seal associated with the proximal end of the sheath and configured to seal the lumen of the sheath around the elongate shaft of the aspiration catheter when the aspiration catheter is in place within the sheath, and wherein the extension conduit is configured to allow fluid from the second fluid source to flow through the lumen of the sheath from the proximal end of the sheath to the distal end of the sheath when the open distal end of the aspiration lumen of the aspiration catheter is extended outside of the lumen of the sheath in a blood vessel and is in proximity to the distal end of the sheath, and when insufficient flowable material is present adjacent the open distal end of the aspiration lumen, such that a negative pressure gradient supplied by the vacuum source further causes a significant volume of the fluid from the second fluid source to actively flow through the aspiration lumen from the open distal end to the proximal end and into an interior of the vacuum source.

In yet another embodiment of the present disclosure, a system for aspirating thrombus includes an aspiration catheter including an elongate shaft configured for placement within a blood vessel of a subject, a supply lumen and an aspiration lumen each extending along the shaft, the supply lumen having a proximal end and a distal end, and the aspiration lumen having a proximal end and an open distal end, and an opening at or near the distal end of the supply lumen, the opening configured to allow the injection of pressurized fluid into the aspiration lumen at or near the distal end of the aspiration lumen when the pressurized fluid is caused or allowed to flow through the supply lumen, a tubing set including a first conduit having a distal end configured to couple to the aspiration lumen of the aspiration catheter and a proximal end configured to couple to a vacuum source, and a second conduit having a distal end configured to couple to the supply lumen of the aspiration catheter and a proximal end configured to couple to a first fluid source, a pressurization element configured to couple to the tubing set and further configured to pressurize fluid from the first fluid source or allow pressurized fluid from the first fluid source to be transferred to the supply lumen, such that the pressurized fluid is capable of flowing through the supply lumen from the proximal end of the supply lumen to the distal end of the supply lumen, a sheath having a proximal end, a distal end and a lumen extending between the proximal end and the distal end, the lumen configured for placement of the aspiration catheter therethrough, the sheath further including an extension conduit in fluid communication with the lumen of the sheath and extending from the sheath, the extension conduit configured for coupling to a second fluid source, the extension conduit fluidly coupled to a valve having a first position configured to selectively couple the extension conduit to a fluid source containing a contrast agent and a second position configured to selectively couple the extension conduit to a fluid source containing substantially no contrast agent, a seal associated with the proximal end of the sheath and configured to seal the lumen of the sheath around the elongate shaft of the aspiration catheter when the aspiration catheter is in place within the sheath, and wherein the aspiration catheter has a first position within the sheath wherein the open distal end of the aspiration lumen of the aspiration catheter is outside of the lumen of the sheath and distal to the distal end of the sheath, and wherein the aspiration catheter has a second position within the sheath wherein the open distal end of the aspiration lumen of the aspiration catheter is within the lumen of the sheath and proximal to the distal end of the sheath.

DETAILED DESCRIPTION OF THE ILLUSTRATED EMBODIMENTS

For the following defined terms, these definitions shall be applied, unless a different definition is given in the claims or elsewhere in this specification.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

Figure 1:
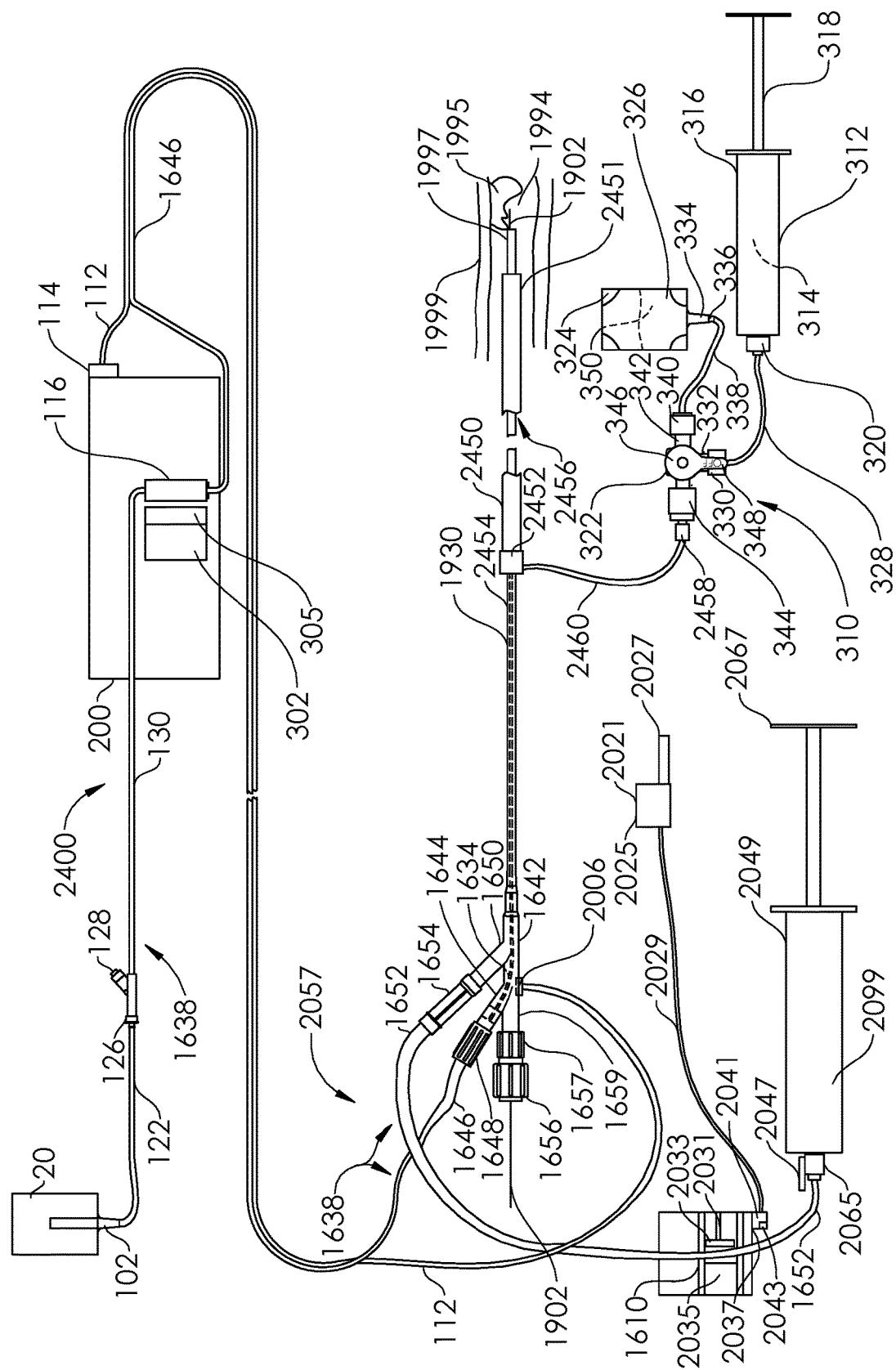
FIG. 1 is a plan view of an aspiration system, according to an embodiment of the present disclosure.
Figure 2:
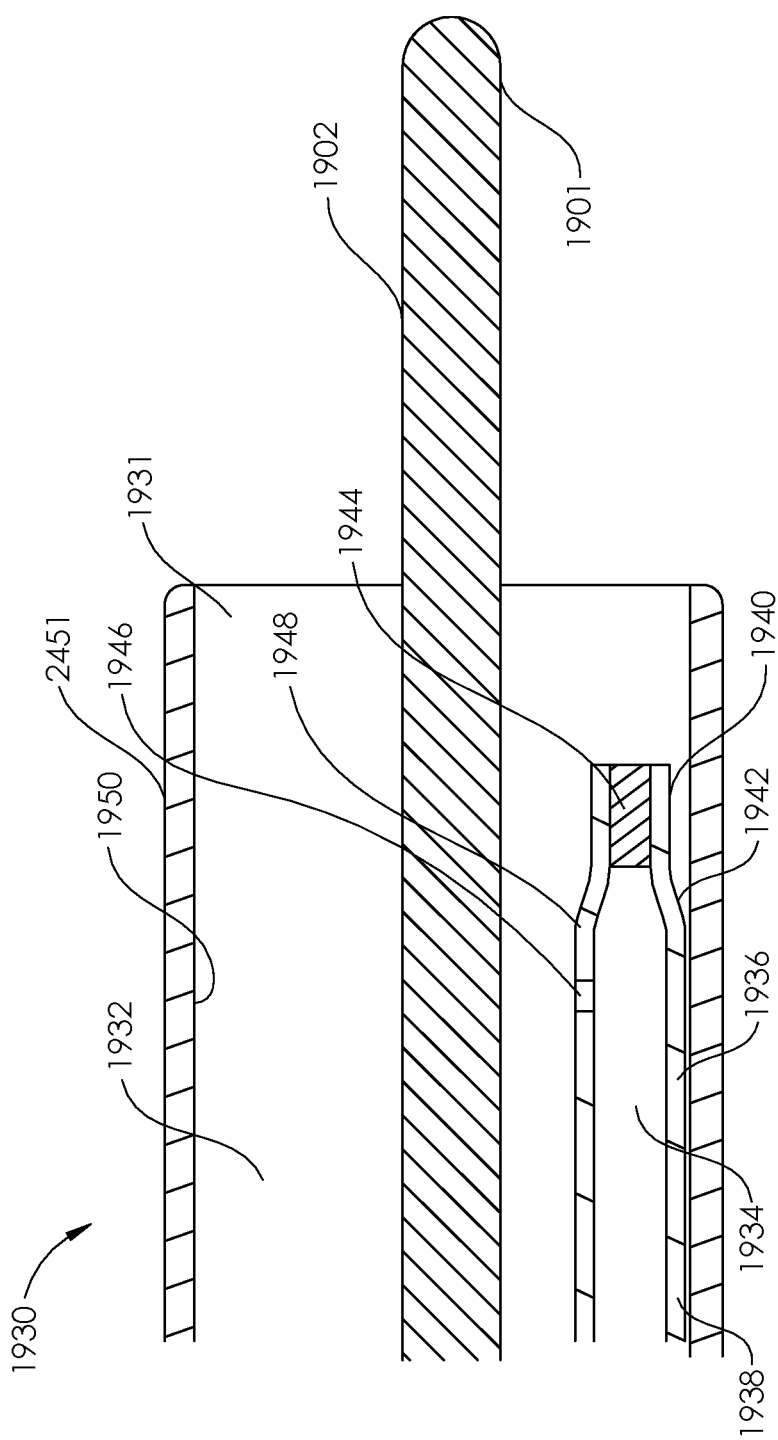
FIG. 2 is a sectional view of the distal end of the aspiration catheter of the system for aspirating thrombus of FIG. 1.
Figure 3:
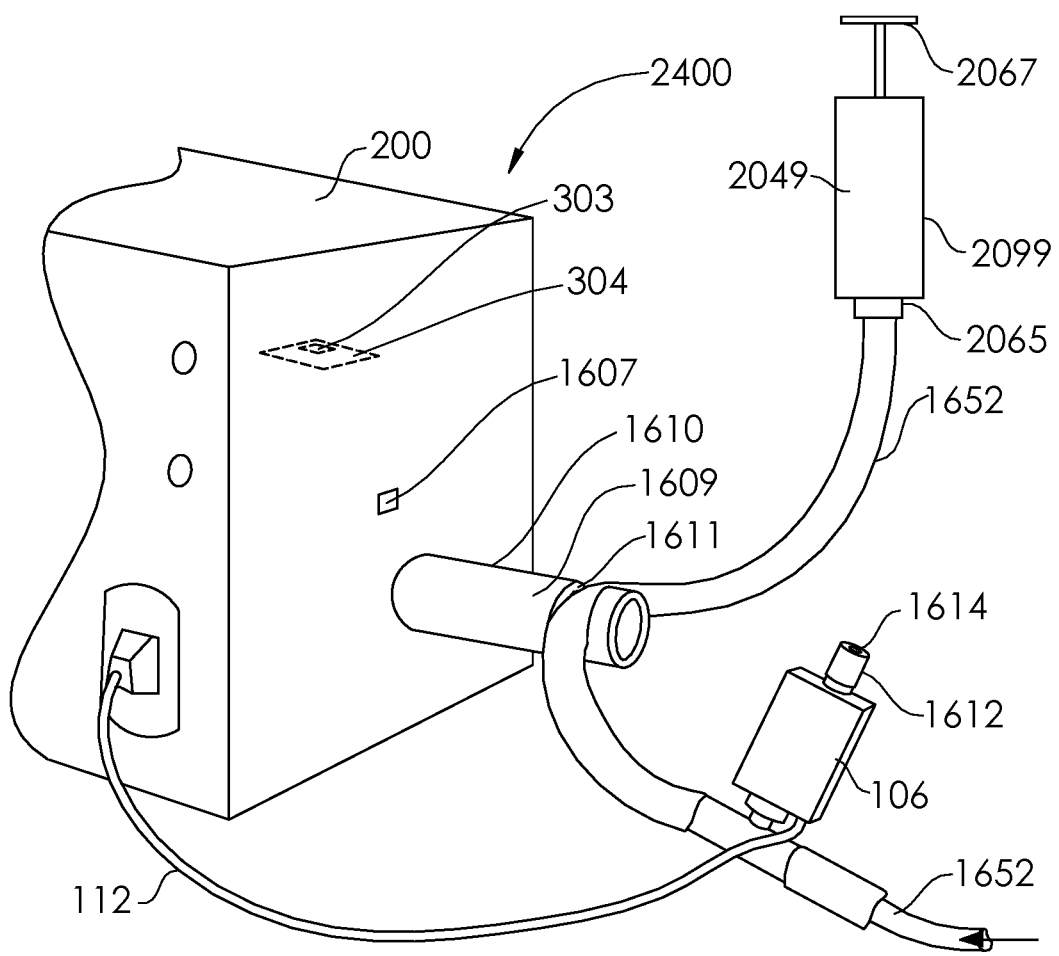
FIG. 3 is a perspective view of a modification of the aspiration system having an alternative pinch valve, according to another embodiment of the present disclosure.

FIGS. 1-3 illustrate a system for aspirating thrombus 2400, including an aspiration catheter 1930, a pump base 200, and a guide sheath 2450. The aspiration catheter 1930 has been inserted through the guide sheath 2450, which includes a proximally-located hemostasis valve 2452 configured for sealing around the shaft 2454 of the aspiration catheter 1930. Alternatively, the hemostasis valve 2452, instead of being part of the guide sheath 2450, may be a separate hemostasis valve that is configured to be coupled to the guide sheath 2450, for example, by a luer fitting or a y-connector. Fluid (e.g., saline) may be injected through the interior lumen 2456 of the guide sheath 2450, and around the shaft 2454 of the aspiration catheter 1930 by attaching a syringe or pump (not shown) to the luer connector 2458 of an extension tube 2460. A guidewire 1902 can be used to track the aspiration catheter 1930 through a patient's vasculature, for example, a blood vessel 1999 having a thrombus 1995. The distal end 2451 of the guide sheath 2450 and the distal end 1997 of the aspiration catheter 1930 are shown in FIG. 1 within the blood vessel 1999 and in relation to the thrombus 1995.

FIG. 2 illustrates the distal end 2451 of the aspiration catheter 1930 and the guidewire 1902. The guidewire 1902 is free to be moved distally or proximally in the longitudinal direction, or to be rotated within the aspiration lumen/guidewire lumen 1932 that extends through the aspiration catheter 1930. The distal end 1901 of the guidewire 1902 may be shapeable, for example, to create a "J"-tip for selectability of vessels or through stenoses or obstructions. A high-pressure injection lumen 1934 is contained within a tube 1936 having a large diameter portion 1938 and a small diameter portion 1940. The small diameter portion 1940 may transition from the large diameter portion 1938 via a neckdown or tapered portion 1942. The small diameter portion 1940 is blocked using a blocking material 1944, which may include a polymer, adhesive, or epoxy adhered to the internal walls of the small diameter portion 1940. Alternatively, the small diameter portion 1940 may be crimped, tied off, sealed, or otherwise occluded, without the use of a blocking material 1944. An orifice 1946 in a wall 1948 of the tube 1936 is configured to create a jet from high pressure fluid injected through the high-pressure injection lumen 1934. The jet exiting the high-pressure injection lumen 1934 through the orifice 1946 and entering the aspiration lumen 1932 is configured to impinge on an inner wall 1950 of the aspiration lumen/guidewire lumen 1932. Aspiration may be performed with the guidewire 1902 in place within the aspiration lumen/guidewire lumen 1932, or may be performed with the guidewire 1902 retracted proximally of the longitudinal location of the orifice 1946, or even with the guidewire 1902 completely removed from the aspiration lumen/guidewire lumen 1932. In cases wherein the guidewire 1902 is left in place (as shown in FIG. 2), during aspiration, the guidewire 1902 may be rotated or otherwise manipulated so that it does not significantly impede the jetting through the orifice 1946, or in some cases, the jet itself may be sufficient to force the guidewire 1902 into a position that does not impede the jetting against the inner wall 1950. The pump base 200 (FIG. 1) is configured to interface with a cassette 116 which is a component of accessories 2057 (part of a tubing set 1638) to pressurize fluid from a fluid source 20. A standard hospital saline bag may be used as fluid source 20; such bags are readily available to the physician and provide the necessary volume to perform the procedure, for example 500 ml or 1,000 ml. In other cases, a saline bottle may be used. A spike 102 can be placed into a septum of the saline bag and communicates with extension tubing 122. Liquid injectate is pumped downstream at the piston pump 305 (or other pump), which pulls more liquid injectate (for example from a saline bag) through a check valve 126 and through a supply tube 130, forcing it into a fluid supply line 1646. An injection port 128 may be used in some cases for injecting other materials such as drugs into the system, or for removing air from the system or priming the system. The spike 102 may be packaged with a removable protective spike cover. Particular configurations of the aspiration catheter 1930, pump base 200, and tubing set 1638 are described in U.S. Pat. No. 9,883,877, issued Feb. 6, 2018, and entitled "Systems and Methods for Removal of Blood and Thrombotic Materials," which is hereby incorporated by reference in its entirety for all purposes.

A connector 1642 is coupled to the aspiration catheter 1930, and includes a female luer sideport 1644 configured to allow injection through the high-pressure injection lumen 1934 of the tube 1936 (FIG. 2) via the fluid supply line 1646. The fluid supply line 1646 includes a male luer 1648, which is connectable to the sideport 1644. The connector 1642 includes a barbed fitting 1650 (sideport) which is configured for attachment of a vacuum line 1652 having a plastic or elastomeric tubular end 1654 configured for sealingly forcing over the barbed fitting 1650. In some embodiments, the barbed fitting 1650 may also include a female luer, so that either the barbed fitting 1650 or the female luer may be chosen as the attachment site. The connector 1642 further includes a Touhy-Borst valve 1656 which may be sealed (closed) if a guidewire 1902 is not used, or may be opened to allow the passage of a guidewire 1902 through the connector 1642 and the aspiration lumen 1932 of the aspiration catheter 1930, and may then be sealed over the guidewire 1902. The Touhy-Borst valve 1656 may include a distal male luer 1657 configured to secure to a female luer 1659 at the proximal end of the connector 1642. In alternate embodiments, the Touhy-Borst valve 1656 may be permanently connected or formed on the connector 1642. The Touhy-Borst valve 1656 is optional, because in some catheter configurations, the clearance around the guidewire at one or more portions of the connector 1642 may be small enough to create sufficient fluid (blood) flow resistance over a length to allow an acceptable hemostasis with little or no backdrip of blood.

Figure 7:
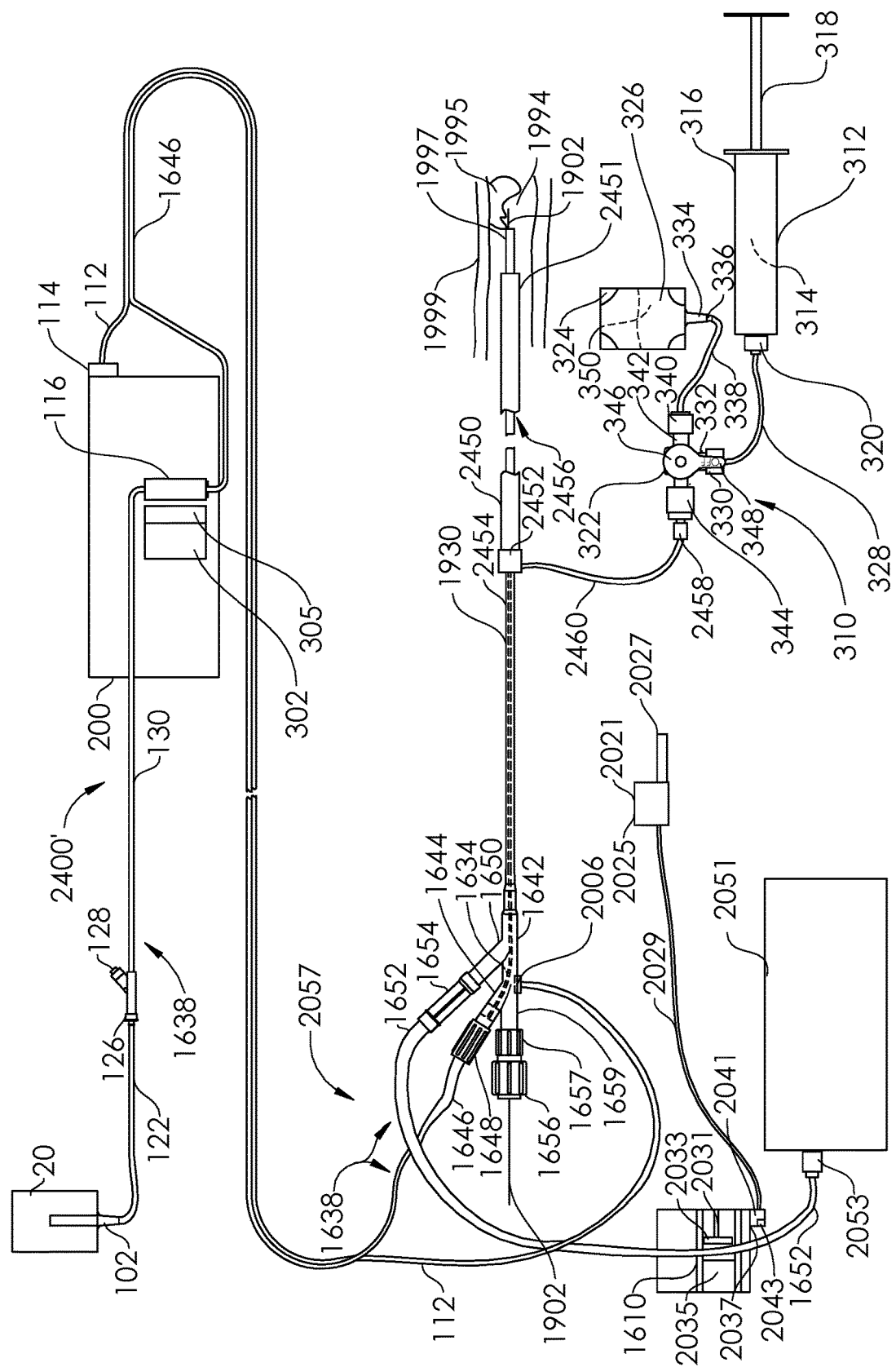
FIG. 7 is a plan view of an alternative aspiration system to the aspiration system of FIG. 1, according to an embodiment of the present disclosure.

Accessories 2057 include a syringe 2049 having a plunger 2067 and a barrel 2099. The syringe 2049 is coupled to the vacuum line 1652 via a luer 2065. The syringe 2049 is configured as a vacuum source, to apply a negative pressure on the aspiration lumen 1932 of the aspiration catheter 1930, for example, to aid in the aspiration of thrombus or other materials from a blood vessel 1999 and into the open distal end 1931 (FIG. 2) of the aspiration lumen 1932. A stopcock 2047, connected between the syringe 2049 and the vacuum line 1652, may be used to maintain the negative pressure gradient, or, the plunger 2067 may be a locking variety of plunger that is configured to be locked in the retracted (vacuum) position with respect to the barrel 2099. Vacuum bottles may be used in place of the syringe 2049, or a vacuum canister, syringe, a vacuum pump or other suitable vacuum or negative pressure sources. A particular alternative vacuum source is shown in the alternative embodiment of FIG. 7. The system for aspirating thrombus 2400' in FIG. 7 is identical to the system for aspirating thrombus 2400 in FIG. 1, but the syringe 2049 is replaced by a vacuum pump 2051. The vacuum pump 2051 is coupled to the vacuum line 1652 by a luer 2053. Thus, in all practicable locations wherein the syringe 2049 is descried herein, the vacuum pump 2051 may alternatively be used.

Returning to FIG. 1, a foot pedal 2021 is configured to operate a pinch valve 1610 for occluding (closing) or opening the vacuum line 1652. The foot pedal 2021 comprises a base 2025 and a pedal 2027, and is configured to be placed in a non-sterile area, such as on the floor, under the procedure table/bed. The user steps on the pedal 2027 causing a signal to be sent along a cable 2029 which is connected via a plug 2041 to an input jack 2037. The input jack 2037 is shown in FIG. 1 remote from the pump base 200, but alternatively may be located on the pump base 200. A circuit board 304 of the pump (FIG. 3) may include a controller 303 configured to receive one or more signals indicating on or off from the foot pedal 2021, either by a direct electrical connection, or wirelessly (remotely). The controller 303 of the circuit board 304 may be configured to cause an actuator 2031 of the pinch valve 1610 to move longitudinally to compress and occlude the vacuum line 1652 between an actuator head 2033 (attached to the actuator 2031) and an anvil 2035, also carried by the pinch valve 1610. By stepping on the pedal 2027, the user is able to thus occlude the vacuum line 1652, stopping the application of a negative pressure from the syringe 2049 onto the aspiration lumen 1932. Also, by stepping on the pedal 2027, the user may cause the opposite action, wherein the actuator head 2033 opens the vacuum line 1652, by moving away from the anvil 2035. The anvil 2035 may have a flat (planar) shape, or a U-shape (e.g., semi-cylindrical), or a V-shape (e.g., a V-block) where it contacts the tubing of the vacuum line 1652. Furthermore or alternatively, the actuator head 2033 itself may have a flat (planar) shape, or a U-shape (e.g., semi-cylindrical), or a V-shape (e.g., a V-block) where it contacts the vacuum line 1652. The foot pedal 2021 may operate by alternately causing the actuator 2031 to move in a first direction and a second, opposite direction, respectively, with alternate applications of the pedal 2027. In some embodiments, when the pedal 2027 of the foot pedal 2021 is depressed, the controller 303 may be configured to open the pinch valve 1610. A pressure transducer 2006 is carried within the female luer 1659 of the connector 1642, but may be alternatively placed at other locations along the aspiration path. The pressure transducer 2006 thus senses a negative pressure and sends a signal to the pump base 200 via a cable 112, causing the controller 303 to start the motor 302 of the pump base 200, which is configured to drive the piston pump 305. The cable 112 includes a connector 114 for connecting electrically to the pump base 200. Because the effect via the electronics is substantially immediate, the motor 302 initiates the piston pump 305 almost immediately after the pedal 2027 is depressed. When the pedal 2027 of the foot pedal 2021 is released, the controller 303 then causes the pinch valve 1610 to close. The pressure transducer 2006 thus senses that no negative pressure is present and causes the motor 302 of the pump base 200 to shut off. Again, the effect via the electronics is substantially immediate, and thus the motor 302 stops operating the piston pump 305 almost immediately after the pedal 2027 is depressed. During sterile procedures, the main interventionalist is usually "scrubbed" such that the user's hands are only intended to touch items in the sterile field. However, the feet/shoes/shoe covers are typically not in the sterile field. Thus, again, a single user may operate a switch (via the pedal 2027) while also manipulating the aspiration catheter 1930, guide sheath 2450, and guidewire 1902. However, this time, it is the sterile field hands and non-sterile field feet that are used. Alternatively, the foot pedal 2021 may comprise two pedals, one configured to command occlusion and one configured to command opening. In an alternative foot pedal embodiment, the pedal 2027 may operate a pneumatic line to cause a pressure activated valve or a cuff to occlude or open the vacuum line 1652, for example, by forcing the actuator head 2033 to move. In another alternative embodiment, the pedal 2027 may turn, slide, or otherwise move a mechanical element, such as a flexible pull cable or push rod that is coupled to the actuator 2031, to move the actuator head 2033. The cable 2029 may be supplied sterile and connected to the base 2025 prior to a procedure. The occlusion and opening of the vacuum line 1652 thus acts as a on and off switch for the pump base 200 (via the pressure sensor 2006), as described in relation to FIG. 1. The on/off function may thus be performed by a user whose hands can focus on manipulating sterile catheters, guidewires, and accessories, and whose foot can turn the motor 302 (and thus pump 305) on and off in a non-sterile environment. This allows a single user to control the entire operation or the majority of operation of the system for aspirating thrombus 2400, 2400'. This can be an advantage both in terms of a rapid, synchronized procedure, but is also helpful in laboratories where additional assistants are not available. The actuator 2031 may be controlled to compress the vacuum line 1652 against the anvil 2035 with a particular force, and the actuator 2031 may be controlled to move at a particular speed, either when compressing or when removing compression. Speed and force control allows appropriate response time, but may also be able to add durability to the vacuum line 1652, for example, by eliminating or reducing overcompression of the vacuum line 1652.

A particular configuration for a system for aspirating thrombus 2400 is illustrated in FIG. 3, and comprises a pump base 200, a vacuum line 1652, and a pressure sensor 106 having a cable 112 for connecting to the pump base 200 and carrying signals from the pressure sensor 106. The other elements of the system for aspirating thrombus 2400 are the same as described in relation to FIG. 1. A pinch valve 1610 is operable by a foot pedal (not shown, but similar to the foot pedal 2021 of the system for aspirating thrombus 2400 in FIG. 1). The foot pedal 2021 may communicate with the pinch valve 1610 via a wired connection through the pump base 200 or may communicate with the pinch valve 1610 wirelessly. The pinch valve 1610 in FIG. 3 extends from the pump base 200 and includes a pinch valve housing 1609 having an opening 1611 which is configured to hold a portion of the vacuum line 1652. Internal to the pinch valve housing 1609 are components equivalent to the actuator head 2033, actuator 2031, and anvil 2035 of the pinch valve 2023 of FIG. 1, which are configured to compress an external portion of the tubing of the vacuum line 1652 when the foot pedal 2021 is depressed. The foot pedal 2021 may then be depressed a second time to release the compression on (decompress) the vacuum line 1652. The compression of the vacuum line 1652 may be configured to be a complete occlusion of the tubing, thus hydraulically isolating the syringe 2049 from the pressure sensor 106. An input port 1612 to the pressure sensor 106 may include a septum 1614 for adding or removing fluid within the vacuum line 1652 (e.g., via a hypodermic needle), or alternatively may include a luer connector and valve. The input port 1612 may also be used to remove air or to allow priming of the system. The pressure sensor 106 is thus configured to reside in a non-sterile field, and is capable of detecting the presence of vacuum (or negative pressure) or the lack of vacuum (or negative pressure) when the foot pedal is depressed by the foot of a user. For example, with the pinch valve 1610 closed via a signal (or resultant mechanical action) from foot pressure on the foot pedal, and thus no vacuum applied within the vacuum line 1606, fluid (such as saline) may be freely injected (proximal to distal) through the aspiration lumen 1932 of the aspiration catheter 1930 connected to the vacuum line 1652, and into the blood vessel 1999 of a patient. The pump base 200 may be configured (via the controller 303) to not pump saline when the lack of vacuum or negative pressure in the vacuum line 1652 is determined. Additionally, if vacuum or negative pressure is present, but is suddenly lost, the pump base 200 will shut down. As seen in FIG. 3, the pinch valve 1610 is located between the syringe 2049 (or other vacuum source) and the pressure sensor 106, thus when the pinch valve 1610 shuts off the aspiration catheter 1930 from the syringe 2049, the pressure sensor 106 is still able to sense the condition within the aspiration lumen 1932 of the aspiration catheter 1930. In most cases, after the pinch valve 1610 is caused to close, the negative pressure within the aspiration lumen 1932 will rise toward the ambient pressure rather quickly. This change will be sensed by the pressure sensor 106. However, in cases in which a piece of thrombus causes a temporary or permanent clog in the aspiration lumen 1932, the pressure sensor 106 is able to sense these occurrences. For example, a large moving thrombus will delay the time that the internal pressure of the aspiration lumen 1932 rises to ambient pressure after the pinch valve 1610 is closed. A complete occlusion of the aspiration lumen 1932 by a thrombus may cause at least some level of negative pressure to remain in the aspiration lumen. Each of these potential occurrences can be identified by the pressure measured by the pressure sensor 106 or by the characteristic of the measured pressure over time. The controller 303 may be configured to send an error or to indicate that there is a temporary or permanent clog in the aspiration lumen 1932, for example, using a display, or a visual, audible, or tactile warning or alarm. The user may respond to this indication by removing and unclogging the aspiration catheter 1930, e.g., by moving a guidewire 1902 back and forth, or may determine that the aspiration catheter 1930 needs to be replaced. Thus, the ability of the pressure sensor 106 to monitor aspiration lumen pressure, regardless of whether the pinch valve 1610 is open or closed, offers an important safety control, as well as a general diagnostic of the state of the system (catheter flow status, etc.). Another general advantage of using a pinch valve 1610 is that blood only contacts the internal luminal wall of the vacuum line 1652, and thus is not forced within interstices of rotatable valves or other moving parts that otherwise could begin to stick or foul with biological material. The vacuum line 1652 is simply compressed an uncompressed, allowing a robust and durable design. The internal volume of the vacuum line 1652 easily maintains sterility. And, as the pinch valve 1610 is isolated from blood/thrombus, it is reusable. As an alternative or in addition to the foot pedal 2021, a push button 1607 may be provided on the pump base 200, or in a remote component. In a first embodiment, the push button 1607 may simply allow manual opening and closing of the pinch valve 1610 on the vacuum line 1652. A first push to compress the vacuum line 1652 and isolate the pressure sensor 106 from the syringe 2049 (and its negative pressure), and a second push to decompress the vacuum line 1652.

Alternatively, the push button 1607 may act as a reset button, and be configured to always open the pinch valve 1610 (when it is closed), or to make no change if the pinch valve 1610 is already open. In an embodiment having both the foot pedal 2021 and the push button 1067, with the push button 1607 configured as a reset button, activation of the foot pedal 2021 toggles the pinch valve 1610 open and closed, while activation of the push button 1607 always places or maintains the pinch valve 1610 in the open position. The push button 1607 may be a mechanical (doorbell) type button, or may be a touch switch (e.g., capacitive, resistive, or piezo), or in some embodiments may even be a toggle or rocker switch. The co-location of two or more of the syringe 2049, the pinch valve 1610, the pump base 200, and the push button 1607 may also be an advantage because it allows a quick assessment by an attending physician or medical personnel in a quick glance, for example, if otherwise focused on catheter manipulation in the sterile field.

An additional advantage supplied by the pinch valve 1610 is that the controller 303 may be configured to cause the piston pump 305 to operate whenever the pinch valve 1610 is in the open condition. Thus, there will always be at least some jet-induced maceration of thrombus while a vacuum is being applied to the aspiration lumen 1932. This minimizes or prevents the aspiration lumen 1932 clogging, which could occur if vacuum or negative pressure is being applied to a large portion of thrombus without any maceration (breaking into smaller pieces).

Returning to FIG. 1, the plug 2041 contains an identification component 2043, which may be read by the circuitry (e.g., circuit board 304) coupled to the input jack 2037. In some embodiments, the identification component 2043 comprises a resistor having a particular value, for example, as part of a Wheatstone bridge. When the plug 2041 is connected to the input jack 2037, the circuitry of the input jack 2037 sends a current through the resistor, resulting in the pump base 200 being electronically placed into a "foot pedal" mode, wherein the foot pedal 2021 can be used to control the operation of the pinch valve 1610. Alternatively, when the plug 2041 is detached from the input jack 2037, and the circuitry is not able to identify the resistor, the pump base 200 is placed in a "manual" mode, wherein the pump 305 is controllable only by buttons (not shown). In other embodiments, instead of a resistor, the identification component 2043 may comprise an RFID (radio-frequency identification) chip, which is read by the circuitry when the plug 2041 is connected to the input jack 2037. In other embodiments, a proximity sensor, such as a Hall-effect device, may be utilized to determine whether the plug 2041 is or is not connected to the input jack 2037.

In should be noted that in certain embodiments, the pinch valve 1610 and the foot pedal 2021 may be incorporated for on/off operation of the pinch valve 1610 on the vacuum line 1652, without utilizing the pressure sensor 106. In fact, in some embodiments, the pressure sensor 106 may even be absent from the system for aspirating thrombus 2400, the foot pedal 2021 being used as a predominant control means.

Returning to FIG. 1, system for aspirating thrombus 2400 further comprises an auxiliary fluid supply system 310 that provides features that improve the efficiency of aspiration procedures performed using the guide sheath 2450 and the aspiration catheter 1930. The auxiliary fluid supply system 310 comprises at least a syringe 312 containing contrast media 314, either non-dilute, or diluted. The contrast media may be diluted 50/50 with normal saline (e.g., heparinized saline), or may be diluted to a ratio of 20% contrast media/80% normal saline. The percentage of contrast may be between about 10% and about 75%, or between about 15% and about 40%. The syringe 312 comprises a barrel 316 and a plunger 318, the barrel comprising a luer 320. The luer 320 may be directly coupled to the luer connector 2458 of the extension tube 2460 of the guide sheath 2450, to allow the interior lumen 2456 of the guide sheath 2450 to have access to the contrast media 314 of the syringe 312. The contrast media 314 allows real-time indication of the status of an aspiration procedure, as will be described. FIG. 1 depicts additional optional elements of the auxiliary fluid supply system 310, including a three-way stopcock 322 and a saline IV bag 324. The saline IV bag 324 may be placed within a pressure bag 326 configured to externally pressurize the internal contents of the saline IV bag 324, for example, to a pressure of 100 mm Hg or higher, or 150 mm Hg or higher, or 200 mm Hg or higher, or 250 mm Hg or higher, or 300 mm Hg or higher, using, for example, a pressure cuff surrounding the saline IV bag 324. The saline IV bag 324 may have a volume of normal saline or heparinized normal saline of 500 ml or 1,000 ml, in common embodiments. The luer 320 of the syringe 312 is coupled to an extension tube 328 having a luer 330 at its distal end. The luer 330 is connected to a first luer 332 of the three-way stopcock 322. The saline IV bag 324 includes a port 334 to which a spike 336 of an extension tube 338 is connected. The extension tube 338 includes a luer 340 at its opposite end which is connector to a second luer 342 of the three-way stopcock 322. A third luer 344 of the three-way stopcock 322 is connected to the luer connector 2458 of the extension tube 2460 of the guide sheath 2450. The three-way stopcock 322 includes a rotatable valve 346 having a projection 348 that is configured to be manipulated by a user to turn the rotatable valve 346. The projection 348 points toward the luer that will be closed (sealed) in that particular configuration. As shown in FIG. 1, the first luer 332 is closed. Thus, the second luer 342 and the third luer 344 are open, allowing the interior lumen 2456 of the guide sheath 2450 to have access to saline 350 within the saline IV bag 324. The saline 350 serves also as a lubricating fluid, so that the system 2400 is self-lubricating. The spike 336 can include a drip chamber, which also allows certain visual feedback. For example, saline in the drip chamber will drip at a higher frequency when the open distal end 1931 of the aspiration lumen 1932 is located within free flowing blood, and will drip slower when the open distal end 1931 is adjacent to or within thrombus, and actively aspirating and/or macerating thrombus, and will drip very little or not at all when the aspiration lumen 1932 is occluded.

In use, the distal end 2451 of the guide sheath 2450 in placed within the blood vessel 1999 via an external puncture or cutdown. For example, via a femoral artery or radial artery. The aspiration catheter 1930 is placed through the guide sheath 2450 and the distal end 1997 of the aspiration catheter 1930 is tracked (e.g., over a guidewire 1902) to a location adjacent a thrombus 1995. The guidewire 1902, if used, may be removed from the aspiration catheter 1930, may be partially retracted, or may be left in place. With the hydraulic connections of FIG. 1 completed, the piston pump 305 is operated to inject high pressure saline through the high-pressure injection lumen 1934, and aspiration is performed through the aspiration lumen 1932 via the evacuated syringe 2049. The pump 305 delivers the high pressure fluid (e.g., saline) through the high-pressure injection lumen 1934 at an injection flow rate $FR_1$. The negative pressure $P_N$ inside the evacuated syringe 2049 creates, independent of the injection flow rate $FR_1$, a potential aspiration flow rate $FR_2$ (e.g., the intended aspiration capacity from purely negative pressure application). With both the negative pressure $P_N$ applied and the injection flow rate $FR_1$ applied, a total potential flow rate $FR_3$ is defined by the equation:

$$FR_3 = FR_1 + FR_2$$

The actual flow rate of the blood/thrombus being aspirated from the blood vessel 1999 may likely be less than the total potential flow rate $FR_3$. But in certain cases, the total potential flow rate $FR_3$ is significantly decreased. For example, if the thrombus 1995 creates a significant occlusion within the blood vessel 1999, and if much or all of the blood or flowable macerated thrombus has been aspirated from the area of interest, there may not be sufficiently enough flowable material adjacent the thrombus 1995 to allow sufficient flow through the aspiration lumen 1932 of the aspiration catheter 1930, even if the aspiration lumen 1932 is not occluded. Thus, a significantly active flowing condition is not present to the extent that new portions of the thrombus 1995 may be sucked inside the open distal end 1931 of the aspiration lumen 1932. In some embodiments, the injection flow rate $FR_1$ is configured to be between about 15 ml/min and about 50 ml/min, or between about 20 ml/min and about 40 ml/min, or between about 25 ml/min and about 35 ml/min. In some embodiments, the potential aspiration flow rate $FR_2$ is configured to be between about 150 ml/min and about 600 ml/min, or between about 300 ml/min and 600 ml/min. or between about 350 ml/min and about 500 ml/min. With the rotatable valve 346 in the position of FIG. 1, the interior lumen 2456 of the guide sheath 2450 is capable of allowing additional saline 350 from the saline IV bag 324 to flow into space 1994 adjacent the thrombus 1995, and adjacent the open distal end 1931 of the aspiration lumen 1932. The new bolus of injected/infused fluid can increase the flowable volume in the space 1994 and can reduce the bulk viscosity of saline/blood/thrombus. The initiation of aspiration at the target thrombus site and entry into the aspiration lumen 1932 of the aspiration catheter 1930 is facilitated. Once the somewhat diluted thrombus begins to flow through the aspiration lumen 1932, the aspiration procedure tends to continue, as it is now in a dynamic state, instead of an initially static state. Thus, changing pressure gradients have caused saline 350 from the saline IV bag 324 to be pulled into the space 1994 automatically, because the pressure inside the saline IV bag 324 is greater than the pressure in the space 1994. Once aspiration flow is recovered and the aspiration of thrombus through the aspiration lumen 1932 resumes, the pressure gradient decreases, and less saline 350 from the saline IV bag 324 will be pulled into the space 1994 in the blood vessel 1999, adjacent the thrombus 1995, again, automatically. The on/off nature of the flow from the saline IV bag 324 and through the interior lumen 2456 of the guide sheath is pressure gradient controlled, and can occur automatically, in order to maintain an active aspiration of thrombus 1995. In the alternative, in the case of a completely clogged aspiration lumen 1932, the actual aspiration flow rate becomes zero. If the actual aspiration flow rate becomes less than the actual injection flow rate, then some injected fluid (saline, etc.) will likely be injected into the blood vessel. This may have negative consequences, such as blood vessel damage, uncontrolled vessel distension, or potentially dangerous thrombus dislodgement. The automatic control of additional injected saline, as described, serves to create an optimized volume during the procedure, analogous in some manner to the cutting fluid that is used in machining of metals. Viscosity is optimized for efficient jet application on the thrombus and aspiration flow.

Figure 4:
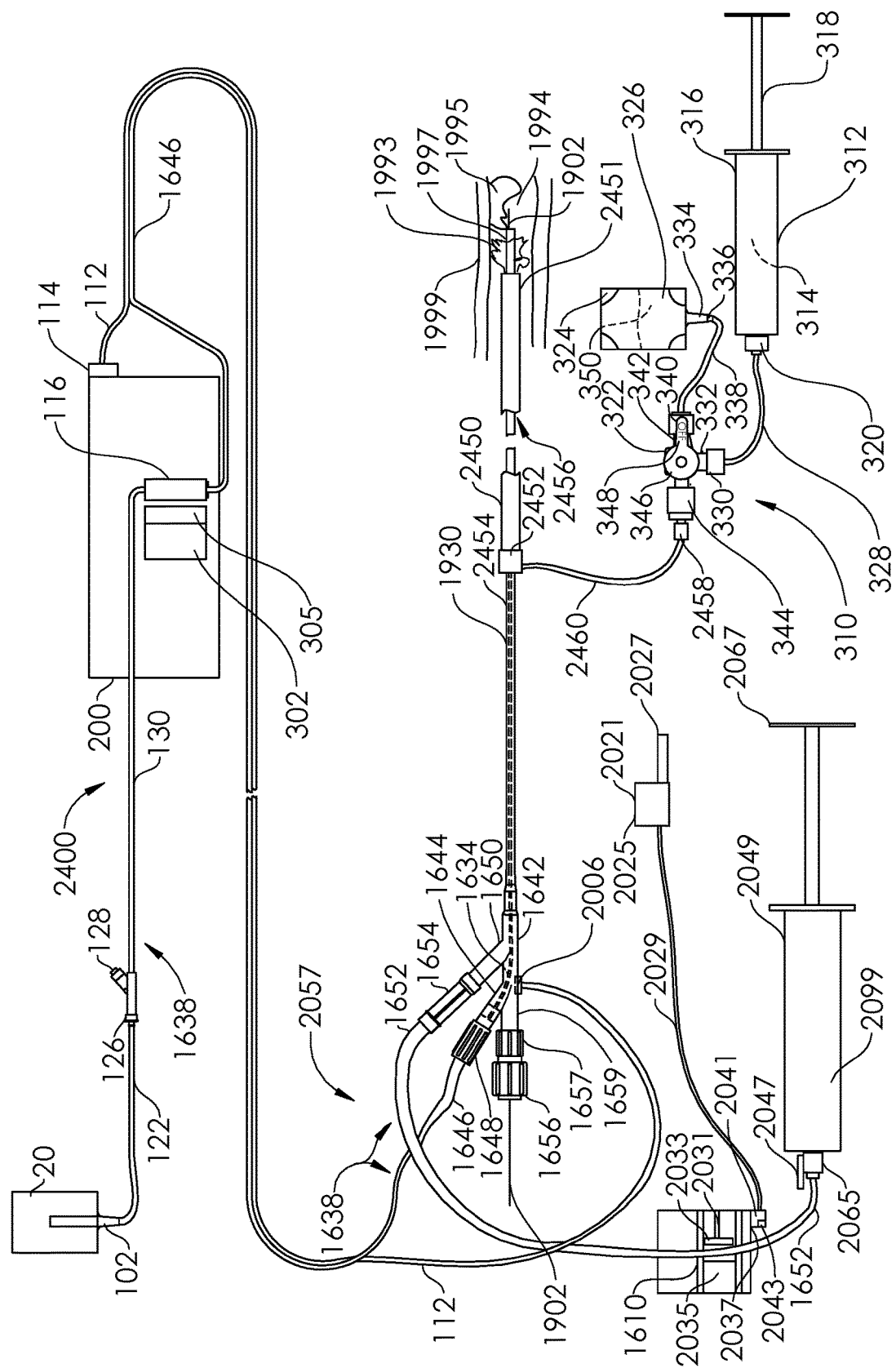
FIG. 4 is plan view of the aspiration system of FIG. 1, in a second condition.

Additional advantages related to the use of the syringe 312 containing contrast media 314 are described in relation to FIG. 4. The rotatable valve 346 has been turned by the user so that the projection 348 points toward the second luer 342, thus closing off access of the saline IV bag 324 and opening access to the syringe 312 containing contrast media 314. Now, when performing the aspiration procedure in the identical manner as that described in relation to FIG. 1, any changes in pressure gradient or changes in available flowable material that cause fluid to flow from proximal to distal through the interior lumen 2456 of the guide sheath 2450, will now pull contrast media 314 from the syringe 312 into the interior lumen 2456 and deliver it into the space 1994. Thus, upon monitoring the procedure by fluoroscopy (e.g., when stepping on the fluoroscopy pedal), injected contrast media 1993, because of its radiopacity, is visible to the user when this change in flow characteristics occurs. The user, thereby receives a visual feedback (e.g., a warning) on fluoroscopy, when key changes to the aspiration process occur. Thus, the status of flow is known by the user. The user is also able to see a maceration zone around the distal end 1997 of the aspiration catheter 1930. The contrast media 1993 itself can improve the aspiration as did the saline, by adding flowable volume and decreasing viscosity (in comparison to thrombus or blood, for example, depending on the particular contrast media, and/or any dilution utilized). However, in many cases, it is desired to control the total amount of contrast media injected during a procedure, to protect the patient's kidneys by reducing the burden on them. Thus, the user may switch the rotatable valve 346 into the position of FIG. 1, to allow saline 350 to be pulled through the interior lumen 2456 of the guide sheath 2450 and into the blood vessel 1999 when the system is in the particular pressure or volume change state. The user may choose to change back and forth between the rotatable valve 346 position of FIG. 1 and of the rotatable valve 346 position of FIG. 4. In alternative embodiments, the plunger 318 of the syringe 312 may be coupled to a mechanical or optical sensor, such as an encoder or linear encoder, that activates an alarm when the plunger 318 moves in relation to the barrel 316. An automated rotating device may even be coupled to the rotatable valve 346 and feedback may be applied by a controller 303, so that sensed movement of the plunger 318 in relation to the barrel 316 greater than a certain distance, greater than a certain velocity, or greater than a certain acceleration cause the rotatable valve 346 to be rotated from the position in FIG. 1, to the position in FIG. 4. This feedback may even be used to activate the fluoroscopy unit, so that the flow of contrast media 314 entering the blood vessel 1999 is immediately shown to the user on the fluoroscopy monitor. The majority of the contrast media 314 entering the blood vessel 1999 would be expected to very low when the aspiration procedure is correctly functioning (no clogs, sufficient flowable material), because any or most of the contrast media 314 injected into the blood vessel 1999 would be aspirated into the aspiration lumen 1932. Thus, the risk of high volumes of contrast added to the blood volume is significantly reduced. Also, with this technique the attending physician would likely not need to check the area of interest for flow (e.g., using angiograms or venograms) as often, thus, further minimizing contrast media 314 injected into the bloodstream of the patient. The method described herein is more efficient and faster than having to stop and "puff" some contrast intermittently. The user may also be able to visualize on fluoroscopy the contrast media 314 specifically moving from the interior lumen 2456 of the guide sheath 2450 to the open distal end 1931 of the aspiration lumen 1930.

Figure 6:
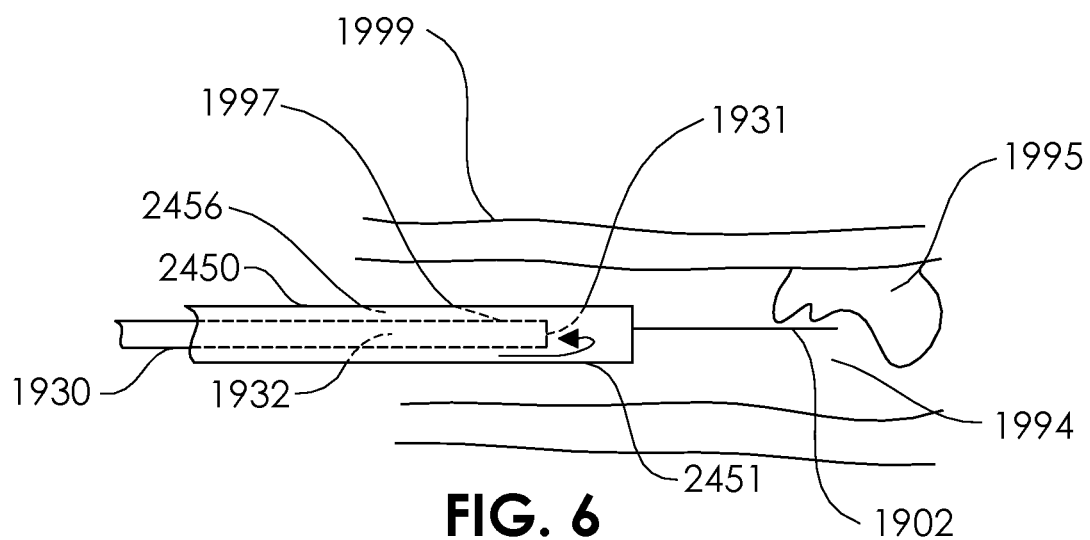
FIG. 6 is a detail view of the distal end of the guide sheath of FIG. 5.
Figure 5:
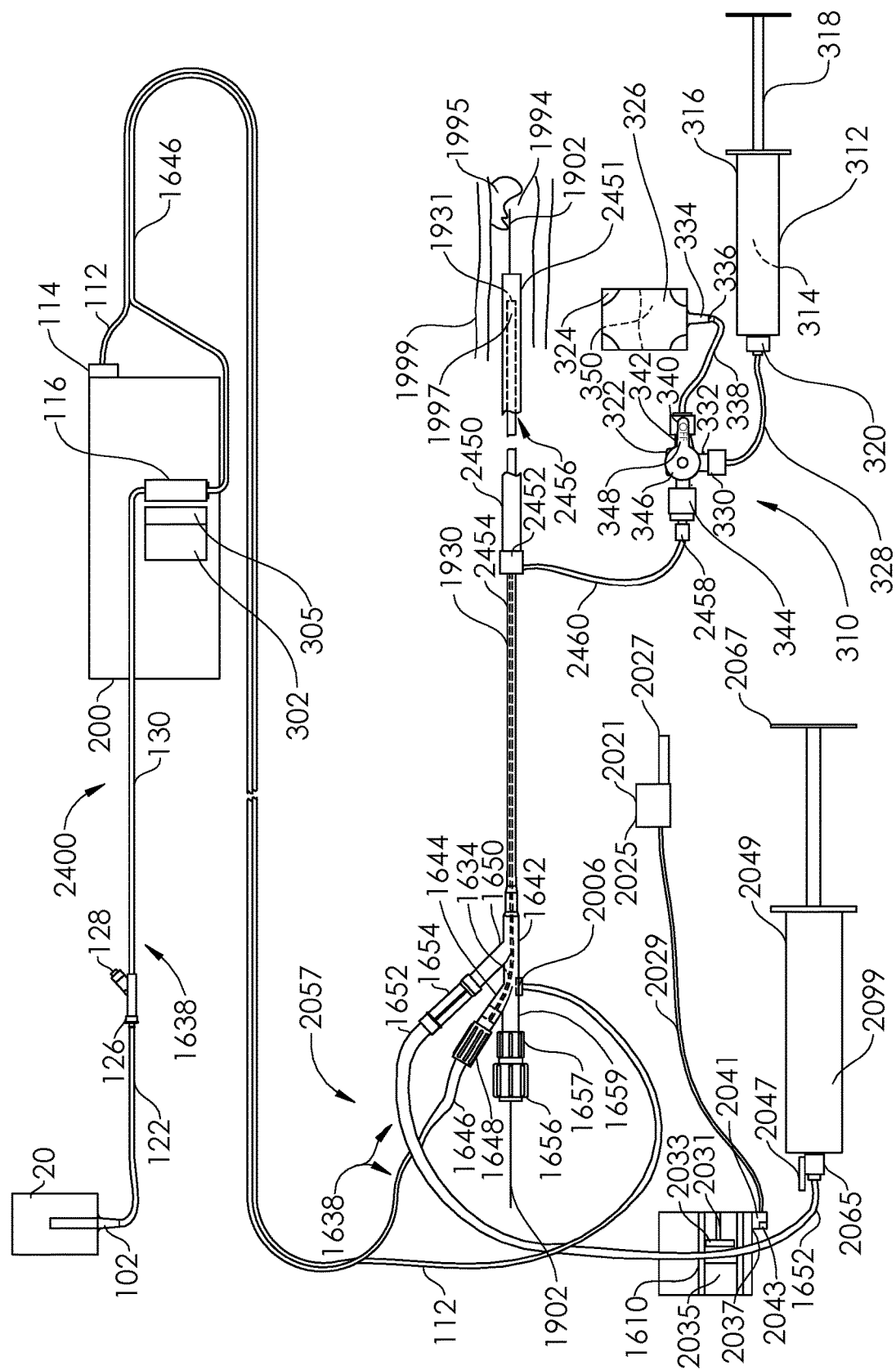
FIG. 5 is plan view of the aspiration system of FIG. 1, in a third condition.

FIG. 5 illustrates the system for aspirating thrombus 2400 with the rotatable valve 346 in the same position as in FIG. 4, but with the open distal end 1931 of the aspiration lumen 1932 of the aspiration catheter 1930 pulled back to that it is entirely within the interior lumen 2456 of the guide sheath 2450. Alternatively, the guide sheath 2450 may be moved distally in longitudinal relation to the aspiration catheter 2450, or they both may be adjusted in relative longitudinal relation. A diagnostic method for assessment of system operation is described in relation to FIG. 5. The user may pull the distal end 1997 of the aspiration catheter 1930 fully into the guide sheath 2450 in this manner, a bit like a turtle pulls its head into its shell, in order to determine particular diagnostics related to the aspiration procedure. In some cases, the aspiration catheter 1930 is pulled back so that the open distal end 1931 of the aspiration lumen 1932 is at least 1 mm within the guide sheath 2450, or at least 2 mm, or at least 3 mm, or at least 4 mm, or at least 5 mm, or at least 6 mm, or at least 7 mm, or at least 8 mm, or at least 9 mm, or at least 10 mm. In some cases, the aspiration catheter 1930 is pulled back so that the open distal end 1931 of the aspiration lumen 1932 is between about 1 mm and about 30 mm within the guide sheath 2450. In some cases, the aspiration catheter 1930 is pulled back so that the open distal end 1931 of the aspiration lumen 1932 is between about 1 mm and about 15 mm within the guide sheath 2450. If the aspiration lumen 1932 is patent, and the contrast media 314 is able to be aspirated through the aspiration lumen 1932, then contrast media 314 will continue being pulled through the interior lumen 2456 of the guide sheath 2450 from proximal to distal, and will be pulled into the open distal end 1931 of the aspiration lumen 1932 (curved arrow, FIG. 6) and through the aspiration lumen 1932 proximal to distal. The plunger 318 of the syringe 312 will be seen by the user contracting into the barrel 316 of the syringe 312 (right to left in FIG. 5). If, however, the aspiration lumen 1932 of the aspiration catheter 1930 is clogged with relatively hard thrombus or one or more other materials, a non-aspiration condition will be demonstrated. The plunger 318 of the syringe 312 will not move in relation to the barrel 316 of the syringe 312. If there is an occlusion of the aspiration lumen 1932, the user is notified by the movement or lack of movement of the plunger 318, and will likely change out the aspiration catheter 1930 for another, or remove the aspiration catheter 1930 and declog the aspiration lumen 1932, for example by a hand injection with a small bore syringe, retrograde (proximal to distal) through the aspiration lumen 1932. Again, in other embodiments, mechanical or optical sensing may be used to automatically determine whether the plunger 318 is moving in relation to the barrel 316 or not, and an alarm or indicator may be broadcast to the user (audible, visual, tactile).

With the advantages of the retrograde flow through the guide sheath 2450, a significantly empty clot bed can fill itself to allow the thrombus 1995 to move, or come in contact with or be closer to the open distal end 1931 of the aspiration lumen 1932. The blood vessel wall can also be distended somewhat, allowing a larger volume of saline and blood within, the further aid the aspiration of thrombus. Using the contrast media 314, real-time visualization can be performed during manipulation (positioning/advancement/retraction) of the aspiration catheter 1930, and of the guide sheath 2450. The plunger 318 can be manually compressed to inject puffs of contrast media 314. Additionally, downstream drug migration can be minimized, if using "clot-busting" drugs injected through or mixed with the saline that is injected through the high pressure injection lumen 1934, because the periods of injection without aspiration (when the aspiration lumen 1932 is blocked) are minimized. Drug may include a lytic agent such as tPA (tissue plasminogen activator) or urokinase. The active use of the lytic agent can actually be more efficient, as less is wasted, and more is delivered to the appropriate target area of action. The lytic agent is delivered to a more dynamic surface area of the thrombus 1995, and is thus more effective in its action on the thrombus 1995. In cases where an active mechanical thrombectomy device is used, the ability to receive injectate from the guide sheath 2450 can serve to cool down a heated catheter tip. Additionally, the used of the contrast media 314 aids in the delineation of the borders of the thrombus 1995. The constant available supply of fluids from the guide sheath 314, both contrast media 314 and saline 350 allow the procedure to be optimized and tailored. Blood loss from excessive aspiration of blood and not thrombus can also be reduced.

Any of the embodiments described herein may be used conjunction with the Apollo™ System (Penumbra, Inc., Alameda, Calif., USA). The aspiration catheters described herein may be replaced by any standard aspiration catheter having one or more aspiration lumens. Aspiration catheters used herein may include the ACE™ or INDIGO® catheters produced by Penumbra, Inc. of Alameda, Calif., USA. The user may pull the distal end 1997 of the aspiration catheter 1930 fully into the guide sheath 2450 to mimic the separator device used in conjunction with the ACE™ or INDIGO® catheters. The coaxially placed tubes/shafts of the guide sheath 2450 and the aspiration catheter 1930 can be moved back and forth longitudinally in relation to each other to create additional shearing of any thrombus in the area, to further macerate the thrombus, or to reposition the thrombus in a more strategically aligned location.

In some instances, a degree of MRI compatibility may be imparted into parts of the devices described herein. For example, to enhance compatibility with Magnetic Resonance Imaging (MRI) machines, it may be desirable to make various portions of the devices described herein from materials that do not substantially distort MRI images or cause substantial artifacts (gaps in the images). Some ferromagnetic materials, for example, may not be suitable as they may create artifacts in an MRI image. In some cases, the devices described herein may include materials that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

In some instances, some of the devices described herein may include a coating such as a lubricious coating or a hydrophilic coating. Hydrophobic coatings such as fluoropolymers provide a dry lubricity. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility.

It should be understood that this disclosure is, in many respects, only illustrative. Changes may be made in details, particularly in matters of shape, size, and arrangement of steps without exceeding the scope of the disclosure. The scope of the disclosure is, of course, defined in the language in which the appended claims are expressed.

While embodiments of the present disclosure have been shown and described, various modifications may be made without departing from the scope of the present disclosure. Embodiments of the present disclosure are contemplated to have utility in a variety of blood vessels, including but not limited to coronary arteries, carotid arteries, intracranial/cerebral arteries, inferior and superior vena cavae and other veins (for example, in cases of deep venous thrombosis or pulmonary embolism), peripheral arteries, shunts, grafts, vascular defects, and chambers of the heart. This includes, but is not limited to, any vessel having a diameter of bout two mm or greater. An aspiration catheter 1930 outer diameter of about seven French or less is contemplated for many of the applications, though in certain applications, it may be larger. In some embodiments, an aspiration catheter 1930 diameter of about six French or less is contemplated. Embodiments of the present disclosure may even be used in non-vascular applications, for example body lumens or cavities having material accumulations that need to be macerated and/or removed.

It is contemplated that various combinations or subcombinations of the specific features and aspects of the embodiments disclosed above may be made and still fall within one or more of the embodiments. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed embodiments. Thus, it is intended that the scope of the present disclosure herein disclosed should not be limited by the particular disclosed embodiments described above. Moreover, while the present disclosure is susceptible to various modifications, and alternative forms, specific examples thereof have been shown in the drawings and are herein described in detail. It should be understood, however, that the present disclosure is not to be limited to the particular forms or methods disclosed, but to the contrary, the present disclosure is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication.

The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. A method for improving a flow condition through a catheter, comprising:

inserting a distal end of a sheath within a vasculature of a subject, the sheath comprising a lumen configured for placement of an aspiration catheter that is configured to be in fluid communication with a first fluid source, the sheath further comprising an extension conduit configured to couple to a second fluid source and a third fluid source, the extension conduit configured to be in fluid communication with the lumen;

placing the aspiration catheter through the sheath and advancing the aspiration catheter such that an open distal end of an aspiration lumen of the aspiration catheter is distal to the distal end of the sheath and is in proximity to a thrombus within a blood vessel of the subject;

selectively fluidly coupling the extension conduit to each of the second fluid source and the third fluid source, the third fluid source comprising a contrast agent;

maintaining fluid in the second fluid source at a pressure of 100 mm Hg or higher to create a pressure gradient between the second fluid source and a space adjacent the thrombus; and activating a pump fluidly communicating with the first fluid source such that pressurized fluid from the first fluid source is applied to a proximal end of a supply lumen of the aspiration catheter to deliver the pressurized fluid to an opening at or near a distal end of the supply lumen for injection of the pressurized fluid into the aspiration lumen at or near a distal end of the aspiration lumen, wherein when an active flowing condition is present, at least some of the thrombus is caused to flow through the aspiration lumen from the open distal end to a proximal end of the aspiration lumen, and into an interior of a vacuum source coupled to the aspiration lumen, and when an active flowing condition is not present, fluid from the second fluid source automatically flows from the second fluid source without a pump disposed between the second fluid source and the sheath, through the lumen of the sheath from a proximal end to a distal end, and to the space adjacent the thrombus to deliver at least some of the fluid from the second fluid source into the blood vessel of the subject until the at least some of the thrombus is caused to flow through the aspiration lumen from the open distal end to the proximal end of the aspiration lumen and the pressure gradient between the second fluid source and the space decreases and the flow of fluid from the second fluid source automatically decreases.

2. The method of claim 1, further comprising:
visualizing on fluoroscopy a portion of the blood vessel at or adjacent the distal end of the sheath as a result of the third fluid source flowing through the lumen of the sheath from the proximal end to the distal end and into the blood vessel.

3. The method of claim 2, when the extension conduit is selectively fluidly coupled to the third fluid source, the third fluid source flowing through the lumen of the sheath from the proximal end to the distal end and into the blood vessel indicates a previous unavailability of flowable material adjacent the thrombus.

4. The method of claim 3, wherein the third fluid source further comprises a syringe having a barrel and plunger longitudinally movable within the barrel, the barrel configured to contain the contrast agent.

5. The method of claim 4, further comprising:
changing the relative longitudinal relationship between the aspiration catheter and the sheath such that the distal end of the aspiration catheter is within the lumen of the sheath and proximal to the distal end of the sheath; and
viewing the plunger of the syringe while the pump is activated, wherein movement of the plunger into the barrel indicates a previous unavailability of flowable material adjacent the open distal end of the aspiration lumen.

6. The method of claim 4, further comprising:
changing the relative longitudinal relationship between the aspiration catheter and the sheath such that the distal end of the aspiration catheter is within the lumen of the sheath and proximal to the distal end of the sheath; and
viewing the plunger of the syringe while the pump is activated, wherein no longitudinal movement of the plunger in relation to the barrel indicates blockage in the aspiration catheter.

7. The method of claim 6, wherein longitudinal movement of the plunger into the barrel indicates active flow through the aspiration catheter.

8. The method of claim 1, when the extension conduit is selectively fluidly coupled to the second fluid source, the second fluid source flowing through the lumen of the sheath from the proximal end to the distal end and into the blood vessel indicates a previous unavailability of flowable material adjacent the open distal end of the aspiration lumen.

9. The method of claim 1, wherein the second fluid source does not comprise a contrast agent.

10. The method of claim 9, wherein the extension conduit is hydraulically coupled to a valve having a first position configured to selectively couple the extension conduit to the third fluid source comprising the contrast agent and a second position configured to selectively couple the extension conduit to the second fluid source.

11. The method of claim 10, further comprising:
placing the valve in the first position; and
visualizing on fluoroscopy a portion of the lumen of the blood vessel at or adjacent the distal end of the sheath as a result of the third fluid source flowing through the lumen of the sheath from the proximal end to the distal end and into the blood vessel.

12. The method of claim 11, wherein the third fluid source flowing through the lumen of the sheath from the proximal end to the distal end and into the blood vessel indicates a previous unavailability of flowable material adjacent the open distal end of the aspiration lumen.

13. The method of claim 11, wherein the third fluid source flowing through the lumen of the sheath from the proximal end to the distal end and into the blood vessel indicates a previous unavailability of flowable material adjacent the thrombus.

14. The method of claim 10, further comprising:
placing the valve in the second position.

15. The method of claim 10, wherein the second fluid source comprises a saline bag.

16. The method of claim 15, wherein the second fluid source further comprises a pressure bag configured to compress the saline bag.

17. The method of claim 16, further comprising:
increasing compression of the pressure bag to a pressure of at least 250 mm Hg.

18. A method for identifying a no flow or low flow condition through a catheter, comprising:
inserting a distal end of a sheath within a vasculature of a subject, the sheath comprising a lumen configured for placement of an aspiration catheter that is configured to be in fluid communication with a first fluid source, the sheath further comprising an extension conduit coupled to a valve having a first position and a second position;
placing the aspiration catheter through the sheath and advancing the aspiration catheter such that an open distal end of an aspiration lumen of the aspiration catheter is in proximity to a thrombus within a blood vessel of the subject;
coupling the valve to at least a second fluid source containing a contrast agent and a third fluid source containing no contrast agent, wherein the first position selectively fluidly couples the extension conduit to the second fluid source containing the contrast agent and wherein the second position selectively fluidly couples the extension conduit to the third fluid source containing no contrast agent;
alternating the valve between the first position to create a pressure gradient between the third fluid source and a space adjacent the thrombus and the second position to create a pressure gradient between the second fluid source and the space adjacent the thrombus; and
activating a pressurization element such that pressurized fluid from the first fluid source is applied to a proximal end of a supply lumen of the aspiration catheter to deliver the pressurized fluid to an opening at or near a distal end of the supply lumen for injection of the pressurized fluid into the aspiration lumen at or near a distal end of the aspiration lumen,
wherein when an active flowing condition is present, at least some of the thrombus is caused to flow through the aspiration lumen from the open distal end to a proximal end, and into an interior of a vacuum source coupled to the aspiration lumen, and when an active flowing condition is not present and the valve is in the first position, fluid from the second fluid source containing the contrast agent is automatically drawn through the lumen of the sheath between a proximal end and a distal end to the space when the pressure associated with the second fluid source is higher than a pressure in the space, and at least some of the fluid from the second fluid source containing the contrast agent is delivered into the blood vessel of the subject to provide visual feedback of a change in flow of the thrombus through the aspiration lumen and an indication of the no flow or low flow condition of the thrombus through the aspiration lumen, and when an active flowing condition is not present and the valve is in the second position, fluid from the third fluid source containing no contrast agent automatically flows through the sheath, without a pump disposed between the third fluid source and the sheath, when the pressure in the third fluid source is higher than the pressure in the space.

19. The method of claim 18, further comprising:
retracting the aspiration catheter so that the open distal end of the aspiration lumen is within the sheath.

20. The method of claim 18, further comprising:
maintaining fluid in the third fluid source containing no contrast agent at a pressure of 100 mm Hg or higher.

\* \* \* \* \*